(12) United States Patent
Waterman

(10) Patent No.: US 12,121,894 B2
(45) Date of Patent: Oct. 22, 2024

(54) MICROFLUIDIC DEVICE

(71) Applicant: Oxford Nanopore Technologies PLC, Oxford (GB)

(72) Inventor: David Waterman, Oxford (GB)

(73) Assignee: Oxford Nanopore Technologies PLC, Oxford (GB)

( * ) Notice: Subject to any disclaimer, the term of this patent is extended or adjusted under 35 U.S.C. 154(b) by 751 days.

(21) Appl. No.: 16/768,642

(22) PCT Filed: Nov. 23, 2018

(86) PCT No.: PCT/GB2018/053391
§ 371 (c)(1),
(2) Date: May 29, 2020

(87) PCT Pub. No.: WO2019/106345
PCT Pub. Date: Jun. 6, 2019

(65) Prior Publication Data
US 2021/0170403 A1      Jun. 10, 2021

(30) Foreign Application Priority Data

Nov. 29, 2017 (GB) .................................... 1719855

(51) Int. Cl.
*B01L 3/00* (2006.01)
*G01N 33/487* (2006.01)

(52) U.S. Cl.
CPC ..... *B01L 3/502715* (2013.01); *B01L 3/50273* (2013.01); *B01L 3/502746* (2013.01);
(Continued)

(58) Field of Classification Search
CPC .......... B01L 3/50; B01L 3/502; B01L 3/5027; B01L 3/502715; B01L 3/50273;
(Continued)

(56) References Cited

U.S. PATENT DOCUMENTS

| 3,799,743 A | 3/1974 | Alexander et al. |
| 4,154,795 A | 5/1979 | Thorne |

(Continued)

FOREIGN PATENT DOCUMENTS

| AU | 2003240941 A1 | 12/2003 |
| CN | 1303147 A | 7/2001 |

(Continued)

OTHER PUBLICATIONS

International Preliminary Report on Patentability for Application No. PCT/GB2018/053391, mail Jun. 11, 2020.
(Continued)

*Primary Examiner* — Ann Montgomery
*Assistant Examiner* — Chau N. B. Tran
(74) *Attorney, Agent, or Firm* — Wolf, Greenfield & Sacks, P.C.

(57) ABSTRACT

A microfluidic device for analysing a test liquid comprises: a sensor (235), such as a membrane provided with nanopores, provided in a sensing chamber (237); a sensing chamber inlet channel (261) and a sensing chamber outlet channel (262), each connecting to the sensing chamber for respectively passing liquid into and out of the sensing chamber, and a reservoir (233) forming a sample input port to the microfluidic device, the reservoir being in fluid communication with the sensing chamber inlet channel (261); a liquid collection channel (232); a barrier (231) between an end of the sensing chamber outlet channel (262) and the liquid collection channel (232); a first seal (251), covering the sample input port; a second seal (252), covering the end of the sensing chamber outlet channel (262), thereby preventing liquid from flowing from the sensing chamber (237), over the barrier (231), into the liquid collection channel (232); wherein the microfluidic device is filled with a liquid from the first seal (251) at the sample input port to the (Continued)

second seal (252), such that the sensor (235) is covered by liquid and unexposed to a gas or gas/liquid interface; and wherein the first and second seals (251, 252) are removable to cause the liquid to flow between the reservoir and the end of the sensing chamber outlet and over the barrier.

10 Claims, 12 Drawing Sheets

(52) U.S. Cl.
CPC ............... *G01N 33/48721* (2013.01); *B01L 2200/0689* (2013.01); *B01L 2200/142* (2013.01); *B01L 2300/043* (2013.01); *B01L 2300/047* (2013.01); *B01L 2300/0636* (2013.01); *B01L 2300/0816* (2013.01); *B01L 2400/0406* (2013.01)

(58) Field of Classification Search
CPC ....... B01L 3/502746; B01L 2200/0689; B01L 2200/142; B01L 2300/043; B01L 2300/047; B01L 220/0636; B01L 2300/0816; B01L 2400/0406; G01N 33/48721
See application file for complete search history.

(56) References Cited

U.S. PATENT DOCUMENTS

| | | | |
|---|---|---|---|
| 4,874,500 | A | 10/1989 | Madou et al. |
| 5,234,566 | A | 8/1993 | Osman et al. |
| 5,403,451 | A | 4/1995 | Riviello et al. |
| 5,503,803 | A | 4/1996 | Brown et al. |
| 6,056,922 | A | 5/2000 | Ikematsu |
| 6,300,141 | B1 | 10/2001 | Segal et al. |
| 6,479,288 | B1 | 11/2002 | Laffafian et al. |
| 6,483,931 | B2 | 11/2002 | Kalnitsky et al. |
| 6,503,452 | B1 | 1/2003 | Boxer et al. |
| 6,699,697 | B2 | 3/2004 | Klemic et al. |
| 6,863,833 | B1 | 3/2005 | Bloom et al. |
| 6,913,697 | B2 | 7/2005 | Lopez et al. |
| 6,916,488 | B1 | 7/2005 | Meier et al. |
| 7,077,939 | B1 | 7/2006 | Crooks et al. |
| 7,144,486 | B1 | 12/2006 | Fritsch et al. |
| 7,169,272 | B2 | 1/2007 | Fritsch et al. |
| 7,294,247 | B1 | 11/2007 | Tian et al. |
| 7,745,116 | B2 | 6/2010 | Williams |
| 7,939,270 | B2 | 5/2011 | Holden et al. |
| 8,124,191 | B2 | 2/2012 | Ervin et al. |
| 8,197,775 | B2* | 6/2012 | Johnston .............. B01L 3/5023 422/402 |
| 8,461,854 | B2 | 6/2013 | Chen et al. |
| 9,057,102 | B2 | 6/2015 | Turner et al. |
| 9,546,400 | B2 | 1/2017 | Turner et al. |
| 9,556,480 | B2 | 1/2017 | Turner et al. |
| 9,613,247 | B2 | 4/2017 | Yang |
| 9,678,056 | B2 | 6/2017 | Turner et al. |
| 9,734,382 | B2 | 8/2017 | Wang et al. |
| 9,738,929 | B2 | 8/2017 | Turner et al. |
| 9,927,398 | B2 | 3/2018 | Reid et al. |
| 10,036,065 | B2 | 7/2018 | Jones |
| 10,215,768 | B2 | 2/2019 | Sanghera et al. |
| 10,338,056 | B2 | 7/2019 | Hyde et al. |
| 10,416,117 | B2 | 9/2019 | Reid et al. |
| 10,549,274 | B2 | 2/2020 | Brown et al. |
| 10,814,298 | B2 | 10/2020 | Hyde et al. |
| 11,084,015 | B2 | 8/2021 | Hyde et al. |
| 11,097,269 | B2 | 8/2021 | Goto et al. |
| 11,561,216 | B2 | 1/2023 | Hyde et al. |
| 11,596,940 | B2 | 3/2023 | Waterman |
| 2002/0074227 | A1 | 6/2002 | Nisch et al. |
| 2002/0123048 | A1 | 9/2002 | Gau |
| 2002/0144905 | A1 | 10/2002 | Schmidt |
| 2003/0015422 | A1 | 1/2003 | Fritsch et al. |
| 2003/0075445 | A1 | 4/2003 | Woudenberg et al. |
| 2003/0098248 | A1 | 5/2003 | Vogel et al. |
| 2003/0111340 | A1 | 6/2003 | Cheng et al. |
| 2003/0148401 | A1 | 8/2003 | Agrawal et al. |
| 2003/0224523 | A1 | 12/2003 | Thornberg et al. |
| 2004/0022677 | A1 | 2/2004 | Wohlstadter et al. |
| 2004/0096358 | A1 | 5/2004 | Blankstein et al. |
| 2004/0171169 | A1 | 9/2004 | Kallury et al. |
| 2005/0014162 | A1 | 1/2005 | Barth et al. |
| 2005/0133101 | A1 | 6/2005 | Chung et al. |
| 2005/0230272 | A1 | 10/2005 | Lee et al. |
| 2005/0279634 | A1 | 12/2005 | Ozaki et al. |
| 2006/0079009 | A1 | 4/2006 | Salmon et al. |
| 2006/0163063 | A1 | 7/2006 | Picollet-Dahan et al. |
| 2006/0194331 | A1 | 8/2006 | Pamula et al. |
| 2006/0257941 | A1 | 11/2006 | McDevitt et al. |
| 2006/0257992 | A1* | 11/2006 | McDevitt .............. B01L 9/527 435/287.2 |
| 2006/0292649 | A1 | 12/2006 | Cahill et al. |
| 2007/0035308 | A1 | 2/2007 | Ide |
| 2007/0161101 | A1 | 7/2007 | Takeuchi |
| 2007/0275480 | A1 | 11/2007 | Brander et al. |
| 2008/0254995 | A1 | 10/2008 | Kim et al. |
| 2009/0072332 | A1 | 3/2009 | Dekker et al. |
| 2009/0142504 | A1 | 6/2009 | Ervin et al. |
| 2009/0167288 | A1 | 7/2009 | Reid et al. |
| 2009/0185955 | A1* | 7/2009 | Nellissen .......... B01L 3/502738 422/68.1 |
| 2010/0035349 | A1* | 2/2010 | Bau .................... G01N 35/0092 422/68.1 |
| 2010/0147450 | A1 | 6/2010 | Takeuchi et al. |
| 2010/0190253 | A1 | 7/2010 | Tazaki et al. |
| 2010/0196203 | A1 | 8/2010 | Sanghera et al. |
| 2010/0264935 | A1 | 10/2010 | Erdman et al. |
| 2010/0304980 | A1 | 12/2010 | Takeuchi et al. |
| 2011/0043234 | A1 | 2/2011 | Lee et al. |
| 2011/0120871 | A1 | 5/2011 | Reid et al. |
| 2011/0121840 | A1 | 5/2011 | Sanghera et al. |
| 2011/0214991 | A1 | 9/2011 | Kim et al. |
| 2011/0274737 | A1 | 11/2011 | Palmaz |
| 2011/0287414 | A1 | 11/2011 | Chen et al. |
| 2011/0318774 | A1 | 12/2011 | Larsen |
| 2012/0010085 | A1 | 1/2012 | Rava et al. |
| 2013/0048499 | A1 | 2/2013 | Mayer et al. |
| 2013/0071932 | A1 | 3/2013 | Itchoda et al. |
| 2013/0140192 | A1 | 6/2013 | Behrends et al. |
| 2013/0196442 | A1 | 8/2013 | Momose et al. |
| 2013/0207205 | A1 | 8/2013 | Chen |
| 2013/0217106 | A1 | 8/2013 | Jones |
| 2013/0270521 | A1 | 10/2013 | Peng et al. |
| 2013/0309776 | A1 | 11/2013 | Drndic et al. |
| 2014/0010735 | A1* | 1/2014 | Tanaka .............. B01L 3/502738 422/504 |
| 2014/0174927 | A1 | 6/2014 | Bashir et al. |
| 2014/0190833 | A1 | 7/2014 | Lieber et al. |
| 2014/0243214 | A1 | 8/2014 | Haga et al. |
| 2014/0255921 | A1 | 9/2014 | Moysey et al. |
| 2014/0296083 | A1 | 10/2014 | Brown et al. |
| 2014/0318964 | A1 | 10/2014 | Dunbar et al. |
| 2014/0329693 | A1 | 11/2014 | Reid et al. |
| 2014/0335512 | A1 | 11/2014 | Moysey et al. |
| 2014/0346059 | A1 | 11/2014 | Akeson |
| 2014/0346515 | A1 | 11/2014 | Yanagi et al. |
| 2014/0371568 | A1 | 12/2014 | Selby et al. |
| 2015/0014160 | A1 | 1/2015 | Hyde et al. |
| 2015/0027885 | A1 | 1/2015 | Rajaraman et al. |
| 2015/0065354 | A1 | 3/2015 | Moysey et al. |
| 2015/0191709 | A1 | 7/2015 | Heron et al. |
| 2015/0198611 | A1 | 7/2015 | Ostrowski et al. |
| 2015/0204763 | A1 | 7/2015 | Stelzle et al. |
| 2015/0218629 | A1 | 8/2015 | Heron et al. |
| 2015/0232923 | A1 | 8/2015 | Drndic et al. |
| 2015/0259724 | A1 | 9/2015 | Guan et al. |
| 2015/0265994 | A1 | 9/2015 | Hyde et al. |
| 2015/0268256 | A1 | 9/2015 | Sanghera et al. |
| 2015/0300986 | A1 | 10/2015 | Reid et al. |
| 2016/0040230 | A1 | 2/2016 | Akeson |
| 2016/0178576 | A1 | 6/2016 | Maney et al. |

(56) References Cited

U.S. PATENT DOCUMENTS

| | | |
|---|---|---|
| 2016/0231307 A1 | 8/2016 | Xie |
| 2016/0257942 A1 | 9/2016 | Bruce et al. |
| 2017/0189906 A1 | 7/2017 | Moll et al. |
| 2017/0326550 A1 | 11/2017 | Brown et al. |
| 2017/0363577 A1 | 12/2017 | Reid et al. |
| 2018/0321188 A1 | 11/2018 | Reid et al. |
| 2018/0372713 A1 | 12/2018 | Stamm et al. |
| 2019/0210021 A1 | 7/2019 | Waterman |
| 2019/0242913 A1 | 8/2019 | Sanghera et al. |
| 2019/0391128 A1 | 12/2019 | Hyde et al. |
| 2020/0292521 A1 | 9/2020 | Xie et al. |
| 2021/0086160 A1 | 3/2021 | Hyde et al. |
| 2021/0300750 A1 | 9/2021 | Waterman |
| 2022/0023819 A1 | 1/2022 | Hyde et al. |
| 2023/0228733 A1 | 7/2023 | Hyde et al. |

FOREIGN PATENT DOCUMENTS

| | | |
|---|---|---|
| CN | 1500555 A | 6/2004 |
| CN | 101078704 A | 11/2007 |
| CN | 100448007 C | 12/2008 |
| CN | 101490277 A | 7/2009 |
| CN | 100571871 C | 12/2009 |
| CN | 102263104 A | 11/2011 |
| CN | 103370617 A | 10/2013 |
| CN | 203466320 U | 3/2014 |
| CN | 103995035 A | 8/2014 |
| CN | 205828393 U | 12/2016 |
| CN | 106457247 A | 2/2017 |
| DE | 102010022929 A1 | 12/2011 |
| EP | 0532215 A2 | 3/1993 |
| EP | 1110084 A1 | 6/2001 |
| EP | 1120469 A2 | 8/2001 |
| EP | 1419818 A1 | 5/2004 |
| EP | 1535667 A1 | 6/2005 |
| EP | 1669746 A1 | 6/2006 |
| EP | 1677102 A1 | 7/2006 |
| EP | 1688742 A1 | 8/2006 |
| EP | 1710578 A1 | 10/2006 |
| EP | 1712909 A1 | 10/2006 |
| EP | 1779921 A1 | 5/2007 |
| EP | 2219032 A1 | 8/2010 |
| GB | 2237390 A | 5/1991 |
| GB | 2446823 A | 8/2008 |
| JP | S5-274882 A | 6/1977 |
| JP | 7307172 A2 | 11/1995 |
| JP | 2004-158330 A2 | 6/2004 |
| JP | 2005-098718 A | 4/2005 |
| JP | 2005-164276 A | 6/2005 |
| JP | 2005-300460 A | 10/2005 |
| JP | 2005-539242 A | 12/2005 |
| JP | 2006-312141 A | 11/2006 |
| JP | 2008-194573 A | 8/2008 |
| JP | 4-215052 B2 | 1/2009 |
| JP | 2009-128206 A | 6/2009 |
| JP | 2010-186677 A2 | 8/2010 |
| JP | 2012-247231 A | 12/2012 |
| JP | 2013-242247 A | 12/2013 |
| JP | 2014-190891 A | 10/2014 |
| JP | 2015-064373 A | 4/2015 |
| KR | 10-2017-0012367 | 2/2017 |
| WO | WO 1988/008534 A1 | 11/1988 |
| WO | WO 1994/025862 A1 | 11/1994 |
| WO | WO 1998/058248 A1 | 12/1998 |
| WO | WO 1999/013101 A1 | 3/1999 |
| WO | WO 2000/013014 A1 | 3/2000 |
| WO | WO 2000/025121 A1 | 5/2000 |
| WO | WO 2000/028312 A1 | 5/2000 |
| WO | WO 2001/059447 A1 | 8/2001 |
| WO | WO 2002/024862 A2 | 3/2002 |
| WO | WO 2002/029402 A2 | 4/2002 |
| WO | WO 2002/082046 A2 | 10/2002 |
| WO | WO 2003/052420 A2 | 6/2003 |
| WO | WO 2005/040783 A1 | 5/2005 |
| WO | WO 2005/124888 A1 | 12/2005 |
| WO | WO 2006/012571 A1 | 2/2006 |
| WO | WO 2006/076703 A2 | 7/2006 |
| WO | WO 2006/100484 A2 | 9/2006 |
| WO | WO 2006/104639 | 10/2006 |
| WO | WO 2006/113550 A2 | 10/2006 |
| WO | WO 2006/138160 A2 | 12/2006 |
| WO | WO 2007/028003 A2 | 3/2007 |
| WO | WO 2007/049576 A1 | 5/2007 |
| WO | WO 2007/116978 A1 | 10/2007 |
| WO | WO 2007/127327 A2 | 11/2007 |
| WO | WO 2007/132002 A1 | 11/2007 |
| WO | WO 2008/012552 A1 | 1/2008 |
| WO | WO 2008/054611 A2 | 5/2008 |
| WO | WO 2008/102120 A1 | 8/2008 |
| WO | WO 2008/102121 A1 | 8/2008 |
| WO | WO 2008/124107 A1 | 10/2008 |
| WO | WO 2008/137008 A2 | 11/2008 |
| WO | WO 2008/156041 A1 | 12/2008 |
| WO | WO 2009/024775 A1 | 2/2009 |
| WO | WO 2009/035647 A1 | 3/2009 |
| WO | WO 2009/077734 A2 | 6/2009 |
| WO | WO 2010/122293 A1 | 10/2010 |
| WO | WO 2010/142954 A1 | 12/2010 |
| WO | WO 2011/046706 A1 | 4/2011 |
| WO | WO 2011/067559 A1 | 6/2011 |
| WO | WO 2011/118211 A1 | 9/2011 |
| WO | WO 2011/154114 A2 | 12/2011 |
| WO | WO 2012/033524 A2 | 3/2012 |
| WO | WO 2012/042226 A2 | 4/2012 |
| WO | WO 2012/107778 A2 | 8/2012 |
| WO | WO 2012/138357 A1 | 10/2012 |
| WO | WO 2013/041878 A1 | 3/2013 |
| WO | WO 2013/057495 A2 | 4/2013 |
| WO | WO 2013/121193 A2 | 8/2013 |
| WO | WO 2013/121224 A1 | 8/2013 |
| WO | WO 2013/123379 A2 | 8/2013 |
| WO | WO 2013/153359 A1 | 10/2013 |
| WO | WO 2014/013260 A1 | 1/2014 |
| WO | WO 2014/019603 A1 | 2/2014 |
| WO | WO 2014/064443 A2 | 5/2014 |
| WO | WO 2014/064444 A1 | 5/2014 |
| WO | WO 2015/183871 A1 | 12/2015 |
| WO | WO 2015/193076 A1 | 12/2015 |
| WO | WO 2016/034591 A2 | 3/2016 |
| WO | WO 2016/059427 A1 | 4/2016 |
| WO | WO 2016/127007 A2 | 8/2016 |
| WO | WO 2016/172724 A1 | 10/2016 |
| WO | WO 2016/187519 A1 | 11/2016 |
| WO | WO 2017/061600 A1 | 4/2017 |
| WO | WO 2018/007819 A1 | 1/2018 |
| WO | WO 2019/063959 A1 | 4/2019 |
| WO | WO 2019/160925 A1 | 8/2019 |
| WO | WO 2020/183172 A1 | 9/2020 |

OTHER PUBLICATIONS

International Search Report and Written Opinion for Application No. PCT/GB2018/053391, mailed Feb. 4, 2019.

[No Author Listed] Avanti Polar Lipids, Inc. Avanti Polar Lipids-Preparations of Liposomes. Www.avantilipids.com 5 pages. Jul. 1, 2014.

Aghdaei et al., Formation of artificial lipid bilayers using droplet dielectrophoresis. Lab Chip. Oct. 2008;8(10):1617-20. doi: 10.1039/b807374k. Epub Aug. 13, 2008.

Anrather et al., Supported membrane nanodevices. J Nanosci Nanotechnol. Jan.-Feb. 2004;4(1-2):1-22.

Astier et al., Toward single molecule DNA sequencing: direct identification of ribonucleoside and deoxyribonucleoside 5'-monophosphates by using an engineered protein nanopore equipped with a molecular adapter. J Am Chem Soc. Feb. 8, 2006;128(5):1705-10.

Baaken et al., Planar microelectrode-cavity array for high-resolution and parallel electrical recording of membrane ionic currents. Lab Chip. Jun. 2008;8(6):938-44. doi: 10.1039/b800431e. Epub Apr. 16, 2008.

Bezrukov et al., Counting polymers moving through a single ion channel. Nature. Jul. 28, 1994;370(6487):279-81.

(56) References Cited

OTHER PUBLICATIONS

Bouaidat et al., Surface-directed capillary system; theory, experiments and applications. Lab Chip. Aug. 2005;5(8):827-36. Epub Jul. 1, 2005.

Bruggemann et al., Microchip technology for automated and parallel patch-clamp recording. Small. Jul. 2006;2(7):840-6.

Bull et al., Polymer Films on Electrodes. J. Electrochem Soc. May 1982;129(5):1009-1015.

Cheng et al., Discrete membrane arrays. J Biotechnol. Sep. 2000;74(3):159-74.

Cheng et al., Single Ion Channel Sensitivity in Suspended Bilayers on Micromachined Supports. Langmuir. 2001;17(4):1240-1242.

Danelon et al., Cell membranes suspended across nanoaperture arrays. Langmuir. Jan. 3, 2006;22(1):22-5.

Estes et al., Electroformation of giant liposomes from spin-coated films of lipids. Colloids Surf B Biointerfaces. May 10, 2005;42(2):115-23.

Fraikin et al., A high-throughput label-free nanoparticle analyser. Nat Nanotechnol. 2011;6(5):308?313. doi:10.1038/nnano.2011.24.

Funakoshi et al., Lipid bilayer formation by contacting monolayers in a microfluidic device for membrane protein analysis. Anal Chem. Dec. 15, 2006;78(24):8169-74.

Garstecki et al., Formation of droplets and bubbles in a microfluidic T-junction-scaling and mechanism of break-up. Lab Chip. Mar. 2006;6(3):437-46. Epub Jan. 25, 2006. Erratum in: Lab Chip. May 2006;6(5):693.

Gonzalez-Perez et al., Biomimetic triblock copolymer membrane arrays: a stable template for functional membrane proteins. Langmuir. 2009;25(18):10447?10450. doi:10.1021/la902417m.

Hasanzadeh et al., Room-temperature ionic liquid-based electrochemical nanobiosensors. Trends Anal Chem. Dec. 2012;41:58-74.

Heron et al., Simultaneous measurement of ionic current and fluorescence from single protein pores. J Am Chem Soc. Feb. 11, 2009;131(5):1652-3. doi: 10.1021/ja808128s.

Hirano et al., Lipid Bilayers at Gel/Gel Interface for Ion Channel Recordings. Surf. Sci. Nanotech. 2008;6:130-133.

Holden et al., Functional bionetworks from nanoliter water droplets. J Am Chem Soc. Jul. 11, 2007;129(27):8650-5. Epub Jun. 16, 2007.

Horn, Avoiding Evaporation. Ibidi. Application Note 12. Mar. 29, 2012, pp. 1-3.

Hovis et al., Patterning and Composition Arrays of Supported Lipid Bilayers by Microcontact Printing. Langmuir. 2001;17:3400-3405.

Ide et al., A novel method for artificial lipid-bilayer formation. Biosens Bioelectron. Oct. 15, 2005;21(4):672-7. Epub Jan. 26, 2005.

Ikariyama et al., Polypyrrole electrode as a detector for electroinactive anions by flow injection analysis. Anal. Chem. 1986, 58, 8, 1803-1806.

Ivanov et al., DNA tunneling detector embedded in a nanopore. Nano Lett. 2011;11(1):279-285. doi:10.1021/nl103873a.

Jeon et al., Long-term storable and shippable lipid bilayer membrane platform. Lab Chip. Oct. 2008;8(10):1742-4. doi: 10.1039/b807932c. Epub Aug. 22, 2008.

Jung et al., Detecting protein-ligand binding on supported bilayers by local pH modulation. J Am Chem Soc. Jan. 28, 2009;131(3):1006-14. doi: 10.1021/ja804542p.

Kam et al., Spatially Selective Manipulation of Supported Lipid Bilayers by Laminar Flow: Steps Toward Biomembrane Microfluidic. Langmuir. 2003;19(5):1624-1631.

Kasianowicz et al., Protonation dynamics of the alpha-toxin ion channel from spectral analysis of pH-dependent current fluctuations. Biophys J. Jul. 1995;69(1):94-105.

Khafizov, Single Molecule Force Spectroscopy Of Single Stranded Dna Binding Protein And Rep Helicase. University of Illinois at Urbana-Champaign Dissertation. 2012.

Kim et al., Liquid-slate field-effect transistors using electrowetting. Applied Physics Letters. 90:043507-1-043507-3.

Krantz Lab. Planar Lip Bilayer Electrophysiology Equipment. Department of Molecular & Cell Biology, University of California, Berkeley. Oct. 6, 2007. Last accessed at mcb.berkeley.edu/labs/krantz/equipment/blm.html on Nov. 26, 2014.

Kung et al., Printing via Photolithography on Micropartitioned Fluid Lipid Membranes. Adv. Materials. 2000;12(10):731-734.

Langecker et al., Synthetic lipid membrane channels formed by designed DNA nanostructures. Science. Nov. 16, 2012;338(6109):932-6. doi: 10.1126/science.1225624.

Le Pioufle et al., Lipid bilayer microarray for parallel recording of transmembrane ion currents. Anal Chem. Jan. 1, 2008;80(1):328-32. Epub Nov. 15, 2007.

Lee et al., Ion channel switch array: A biosensor for detecting multiple pathogens. Industrial Biotechnology. May 2005;1(1):26-31. doi:10.1089/ind.2005.1.26.

Lee et al., Nanoarrays of tethered lipid bilayer rafts on poly(vinyl alcohol) hydrogels. Lab Chip. Jan. 7, 2009;9(1):132-9. doi: 10.1039/b809732a. Epub Oct. 22, 2008.

Lee et al., Polyelectrolyte Micropatterning Using Agarose Plane Stamp and a Substrate Having Microscale Features on Its Surface. Bull. Korean Chem. Soc., vol. 26(10):1539-1542 (2005).

Lewis et al., The Mesomorphic Phase Behavior of Lipid Bilayers. Structure Biological Membranes. 3rd Ed. Ed: Yeagle. CRC Press 2011. 19-89.

Li et al., Microfluidic system for planar patch clamp electrode arrays. Nano Lett. Apr. 2006;6(4):815-9.

Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.

Luan et al., Base-by-base ratcheting of single stranded DNA through a solid-state nanopore. Phys Rev Lett. Jun. 10, 2010;104(23):238103. Epub Jun. 10, 2010.

Mach et al., Miniaturized planar lipid bilayer: increased stability, low electric noise and fast fluid perfusion. Anal Bioanal Chem. Feb. 2008;390(3):841-6. Epub Oct. 31, 2007.

Majd et al., Hydrogel stamping of arrays of supported lipid bilayers with various lipid compositions for the screening of drug-membrane and protein-membrane interactions. Angew Chem Int Ed Engl. Oct. 21, 2005;44(41):6697-700.

Malmstadt et al., Automated formation of lipid-bilayer membranes in a microfluidic device. Nano Lett. Sep. 2006;6(9):1961-5.

Mangold et al., Reference electrodes based on conducting polymers. Fresenius J Anal Chem. Jun. 2000;367(4):340-2.

Mastrangeli et al., Challenges for Capillary Self-Assembly of Microsystems. IEEE Transactions. Jan. 2011;1(1):133-149.

Mastrangeli et al., Self-assembly from milli- to nanoscales: methods and applications. J Micro Microeng. 2009; 19:083001.

Maurer et al., Reconstitution of ion channels in agarose-supported silicon orifices. Biosens Bioelectron. May 1, 20075;22(11):2577-84. Epub Nov. 13, 2006.

McAlduff et al., Freestanding lipid bilayers as substrates for electron cryomicroscopy of integral membrane proteins. J Microsc. Feb. 2002;205(Pt 2):113-7.

Montal et al., Formation of bimolecular membranes from lipid monolayers and a study of their electrical properties. Proc Natl Acad Sci U S A. Dec. 1972;69(12):3561-6.

Moran-Mirabal et al., Micrometer-sized supported lipid bilayer arrays for bacterial toxin binding studies through total internal reflection fluorescence microscopy. Biophys J. Jul. 2005;89(1):296-305. Epub Apr. 15, 2005.

Ogier et al., Suspended Planar Phospholipid Bilayers on Micromachined Supports, Langmuir, vol. 16:5696-5701 (2000).

Onoe et al., Three-Dimensional Micro-Self-Assembly Using Hydrophobic Interaction Controlled by Self-Assembled Monolayers. J Micro Systems. Aug. 2004;13(4):603-611.

Parthasarathy et al., Protein patterns at lipid bilayer junctions. Proc Natl Acad Sci U S A. Aug. 31, 2004;101(35):12798-803. Epub Aug. 20, 2004.

Peterman et al., "Ion Channels and Lipid Bilayer Membranes Under High Potentials Using Microfabricaled Apertures," Biomedical Microdevices, vol. 4(3):231-236 (2002).

Polk et al., Ag/AgCl microelectrodes with improved stability for microfluidics, Sensors and Actuators B., vol. 114:239-247 (2006).

(56) References Cited

OTHER PUBLICATIONS

Rauf et al., Studies on sildenafil citrate (Viagra) interaction with DNA using electrochemical DNA biosensor. Biosens Bioelectron. May 15, 2007;22(11):2471-7. Epub Nov. 7, 2006.
Romer et al., Impedance analysis and single-channel recordings on nano-black lipid membranes based on porous alumina. Biophys J. Feb. 2004;86(2):955-65.
Sackmann, Supported membranes: scientific and practical applications. Science. Jan. 5, 1996;271(5245):43-8.
Sandison et al., Rapid fabrication of polymer microfluidic systems for the production of artificial lipid bilayers. J. Micromech. Microeng., vol. 15:S139-S144 (2005).
Sandison et al., Air-exposure technique for the formation of artificial lipid bilayers in microsystems. Langmuir. Jul. 17, 2007;23(15):8277-84. Epub Jun. 22, 2007.
Sapra et al., Lipid-coated hydrogel shapes as components of electrical circuits and mechanical devices. Sci Rep. 2012;2:848. doi: 10.1038/srep00848. Epub Nov. 14, 2012.
Sarles et al., Bilayer formation between lipid-encased hydrogels contained in solid substrates. ACS Appl Mater Interfaces. Dec. 2010;2(12):3654-63. doi: 10.1021/am100826s. Epub Nov. 10, 2010.
Schindler et al., Branched bimolecular lipid membranes. Biophys J. Sep. 1976; 16(9):1109-13.
Schmidt et al., A Chip-Based Biosensor for the Functional Analysis of Single Ion Channels. Angew Chem Int Ed Engl. Sep. 1, 2000;39(17):3137-3140.
Shim et al., Stochastic sensing on a modular chip containing a single-ion channel. Anal Chem. Mar. 15, 2007;79(6):2207-13. Epub Feb. 9, 2007.
Smith et al., Micropatterned fluid lipid bilayer arrays created using a continuous flow microspotter. Anal Chem. Nov. 1, 2008;80(21):7980-7. doi: 10.1021/ac800860u. Epub Oct. 8, 2008.
Soni et al., Synchronous optical and electrical detection of biomolecules traversing through solid-state nanopores. Rev Sci Instrum. Jan. 2010;81(1):014301. doi: 10.1063/1.3277116.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Sun et al., Microfluidic static droplet arrays with tuneable gradients in material composition. Lab Chip. Dec. 7, 2011;11(23):3949-52. doi: 10.1039/c11c20709a. Epub Oct. 12, 2011.
Suzuki et al., Highly reproducible method of planar lipid bilayer reconstitution in polymethyl methacrylate microfluidic chip. Langmuir. Feb. 14, 2006;22(4):1937-42.
Suzuki et al., Planar lipid bilayer reconstitution with a micro-fluidic system. Lab Chip. Oct. 2004;4(5):502-5. Epub Sep. 2, 2004.
Suzuki et al., Planar Lipid Membrane Array for Membrane Protein Chip. 17th IEEE International Conference on Micro Electro Mechanical Systems (MEMS), pp. 272-275 (2004).
Syms et al., Surface Tension-Powered Self-Assembly of Microstructures—The State of the Art. J Micro Systems. Aug. 2003;12(4):387-417.
Third Party Submission Under 37 CFR 1.290 for U.S. Appl. No. 14/302,287 dated May 19, 2016.
Thorsen et al., Dynamic pattern formation in a vesicle-generating microfluidic device. Phys Rev Lett. Apr. 30, 2001;86(18):4163-6.
Urisu et al., Formation of high-resistance supported lipid bilayer on the surface of a silicon substrate with microelectrodes. Nanomedicine. Dec. 2005;1(4):317-22.
Vidinha et al., Ion jelly: a tailor-made conducting material for smart electrochemical devices. Chem Commun (Camb). Nov. 30, 2008;(44):5842-4. doi: 10.1039/b811647d. Epub Oct. 3, 2008.
Vulto et al., Microfluidic channel fabrication in dry film resist for production and prototyping of hybrid chips. Lab Chip. Feb. 2005;5(2):158-62. Epub Dec. 3, 2004.
Wagterveld et al., Ultralow hysteresis superhydrophobic surfaces by excimer laser modification of SU-8. Langmuir. Dec. 19, 2006;22(26):10904-8.
Watanabe et al., Electrical recording of Nanopore membrane proteins in a microfluidic device. The Papers of Technical Meeting on Bio Micro Systems, IEE Japa. 2010; BMS-10(7-27):5-8.
Yusko et al., Controlling the translocation of proteins through nanopores with bioinspired fluid walls. Nat Nanotechnol. Apr. 2011;6(4): 253-260. EPub Feb. 20, 2011. doi: 10.1038/nnano.2011.12.
Zagnoni et al., Bilayer lipid membranes from falling droplets. Anal Bioanal Chem. Mar. 2009;393(6-7):1601-5. doi:10.1007/s00216-008-2588-5. Epub Jan. 19, 2009.
Zagnoni et al., Controlled delivery of proteins into bilayer lipid membranes on chip. Lab Chip. Sep. 2007;7(9):1176-83. Epub Jun. 27, 2007.
Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.
Third Party Observations for EP 17739663.7, mailed Sep. 23, 2021. 18 pages.
U.S. Appl. No. 16/816,221, filed Mar. 11, 2020, Xie et al.
PCT/GB2018/053391, dated Feb. 4, 2019, International Search Report and Written Opinion.
PCT/GB2018/053391, dated Jun. 11, 2020, International Preliminary Report on Patentability.
Hromada et al., Single molecule measurements within individual membrane-bound ion channels using a polymer-based bilayer lipid membrane chip. Lab Chip. Apr. 2008;8(4):602-8. doi:10.1039/b716388f. Epub Feb. 29, 2008.
Third Party Observations for Application No. EP21749248.7, mailed Jul. 12, 2023.
U.S. Appl. No. 18/459,592, filed Sep. 1, 2023, Xie et al.

\* cited by examiner

MICROFLUIDIC DEVICE

RELATED APPLICATIONS

This Application is a national stage filing under 35 U.S.C. 371 of international application number PCT/GB2018/053391, filed Nov. 23, 2018, which claims the benefit of United Kingdom application number 1719855.7, filed Nov. 29, 2017, each of which is herein incorporated by reference in its entirety.

FIELD OF THE DISCLOSURE

The present invention relates to a microfluidic device, in particular a device comprising a sensor for sensing in wet conditions.

BACKGROUND

A variety of microfluidic devices and sensors are known. Sensors such as disclosed by WO99/13101 and WO88/08534 are provided in the dry state and a liquid test sample applied to the device is transported to the sensor region within the device by capillary flow. Other types of sensors are known, such as ion selective sensors comprising an ion selective membrane.

Another example is provided by WO 2009/077734 which discloses an apparatus for creating layers of amphiphilic molecules, and is now briefly discussed with reference to FIG. 1.

FIG. 1 shows an apparatus 1 which may be used to form a layer of amphiphilic molecules. The apparatus 1 includes a body 2 having layered construction comprising a substrate 3 of non-conductive material supporting a further layer 4 also of non-conductive material. A recess 5 is formed in the further layer 4, in particular as an aperture which extends through the further layer 4 to the substrate 3. The apparatus 1 further includes a cover 6 which extends over the body 2. The cover 6 is hollow and defines a chamber 7 which is closed except for an inlet 8 and an outlet 9 each formed by openings through the cover 6. The lowermost wall of the chamber 7 is formed by the further layer 4.

In use aqueous solution 10 is introduced into the chamber 7 and a layer of amphiphilic molecules is formed across the recess 5 separating aqueous solution 10 in the recess 5 from the remaining volume of aqueous solution in the chamber 7. Use of a chamber 7 which is closed makes it very easy to flow aqueous solution 10 into and out of the chamber 7. This is done simply by flowing the aqueous solution 10 through the inlet 8 as shown in FIG. 1 until the chamber 7 is full. During this process, gas (typically air) in the chamber 7 is displaced by the aqueous solution 10 and vented through the outlet 9.

The apparatus includes an electrode arrangement to allow measurement of electrical signals across the layer of amphiphilic molecules, which allows the device to function as a sensor. The substrate 3 has a first conductive layer 20 deposited on the upper surface of the substrate 3 and extending under the further layer 4 to the recess 5. The portion of the first conductive layer 20 underneath the recess 5 constitutes an electrode 21 which also forms the lowermost surface of the recess 5. The first conductive layer 20 extends outside the further layer 4 so that a portion of the first conductive layer 20 is exposed and constitutes a contact 22.

The further layer 4 has a second conductive layer 23 deposited thereon and extending under the cover 6 into the chamber 7, the portion of the second conductive layer 23 inside the chamber 7 constituting an electrode 24. The second conductive layer 23 extends outside the cover 6 so that a portion of the second conductive layer 23 is exposed and constitutes a contact 25. The electrodes 21 and 24 make electrical contact with aqueous solution in the recess 5 and chamber 7. This allows measurement of electrical signals across the layer of amphiphilic molecules by connection of an electrical circuit to the contacts 22 and 25.

In practice, the device of FIG. 1 can have an array of many such recesses 5. Each recess is provided with the layer of amphiphilic molecules. Further, each layer can be provided with a nanopore, to allow other molecules to pass through the layer (which affects the electrical signal measured). For example, one nanopore is provided per membrane. The extent to which this occurs is determined in part upon the concentration of the nanopores in the medium applied to the membranes.

An analysis apparatus incorporating means to provide amphiphilic membranes and nanopores to the sensor is disclosed by WO2012/042226. The step of providing the amphiphilic membranes and nanopores is carried out prior to use of the device, typically by the end user. However this provides drawbacks in that additional steps are required on the part of the consumer and also requires the provision of an apparatus with a complex fluidic arrangement including valves and supply reservoirs. Furthermore setting up such a sensor for use by the user can be prone to error. There is a risk that, even if the system is set up correctly, it will dry out, which could potentially damage the sensor. There is also a risk that excessive flowrates in the sample chamber could cause damage to the sensor. This risk increases for more compact devices, which bring the sample input port into closer proximity to the sensor (and so there is less opportunity for system losses to reduce the flowrates through the device).

It is therefore desirable to provide a device to the user in a 'ready to use' state wherein the amphiphilic membranes and nanopores are pre-inserted and are maintained under wet conditions. More generally it is also desirable to provide a device wherein the sensor is provided in a wet condition, for example provided in a wet condition to or by the user prior to detection of an analyte.

A typical nanopore device provided in a 'ready to use' state comprises an array of amphiphilic membranes, each membrane comprising a nanopore and being provided across a well containing a liquid. Such a device and method of making is disclosed by WO2014/064443. Test liquid to be analysed is applied to the upper surface of the amphiphilic membranes. Providing a device in a 'ready to use' state however has additional considerations in that care needs to be taken that the sensor does not dry out, namely that liquid is not lost from the well by passage through the amphiphilic membrane, which may result in a loss of performance or damage the sensor. One solution to address the problem of drying out of the sensor is to provide the device with a buffer liquid over the surface of the amphiphilic membrane such that any evaporation through the surface of the membrane is minimised and the liquids provided on either side of the membrane may have the same ionic strength so as to reduce any osmotic effects. In use the buffer liquid may be removed from the surface of the amphiphilic membrane and a test liquid to be analysed is introduced to contact the surface. When the device contains a buffer liquid, the questions of how to remove it and how to introduce the test liquid become an issue. Due to the presence of the buffer liquid, namely that the sensor is provided in a 'wet state', the capillary force provided by a dry capillary channel cannot be utilised to draw test liquid into the sensor. A pump may be used to displace the buffer liquid and to introduce a test liquid, however this results in a device with added complexity and cost.

An ion selective electrode device comprising one or more ion selective membranes is typically calibrated prior to use with a solution having a known ionic concentration. The ion selective membranes may be provided in a capillary flow path connecting a fluid entry port through which a calibrant solution may be introduced and caused to flow over the ion selective electrodes by capillary action. Thereafter the calibrant solution may be displaced and the analyte solution caused to flow over the electrodes in order to perform the measurement. In large benchtop devices for the measurement of ions, a peristaltic pump may for example be employed to displace the liquid. However for simple disposable devices, a less complex solution is more desirable.

In other devices, a pair of electrodes may be provided in a capillary channel into which a first test liquid is drawn by capillary action in order to make an electrochemical analysis. Following measurement of the first test liquid, it may be desirable to measure a second test liquid. However an additional force intervention is needed in order to remove the first test liquid prior to introduction of the second test liquid as capillary force is longer available.

PCT/GB2017/052910, incorporated herein by reference, discloses an apparatus 100 which may be used to form a layer of amphiphilic molecules, similar to that of FIGS. 1 and 2, and it is shown in FIG. 10. However, in contrast to FIGS. 1 and 2, the apparatus 100 of FIG. 10 is made of detachable components. As such, the constituent components of apparatus 100 may be provided as a kit.

A first component 110 forms the base of the device 100, whilst a second component 120 can be inserted and removed from the base component 110. The base component 110 itself can be composed of multiple components 111, 112. When inserted, the first and second components 110, 120 form a connection between first and second arrays of electrical connectors (discussed further below). This allows multiple second components to be used with a single base component 110. The body of the second component is typically made of a plastic material having a degree of elasticity. The plastic material may for example be polycarbonate.

In the device of FIG. 10, a disposable flow-cell is provided as the second component 120. The flow cell can be equivalent to that discussed in WO 2014/064443, which is hereby incorporated in its entirety by reference. In the arrangement of FIG. 4, the ability to provide a disposable flow-cell 120 means that more expensive components of the analysis device 100 can be incorporated into the first component 110, making it possible to perform multiple experiments with different flow-cells 120 relatively cheaply. As such, the flow-cell 120 may comprise corresponding features to the recesses and apertures 5 described in respect of FIG. 1 and FIG. 2.

In view of the forgoing, there remains a challenge to provide an easy to use microfluidic device that can be disposable or reusable, whilst supplied in a manner that is ready to use.

SUMMARY

The present invention aims to at least partly reduce or overcome the problems discussed above.

According to an aspect of the invention, there is provided a microfluidic device for analysing a test liquid comprising one or more of: a bridgeable barrier an upstream portion, positioned upstream from the bridgeable barrier, for housing a sensor provided in a sensing chamber and for receiving a test liquid to be analysed, said upstream portion comprising an inlet channel and an outlet channel, and being fillable with a liquid between the inlet channel and the outlet channel; a downstream portion, positioned downstream from the bridgeable barrier, for receiving liquid from the outlet channel of the upstream portion; a removably attachable seal, configured to enclose the upstream portion and, when a liquid is provided in the upstream portion, inhibit flow of the liquid before removal of the seal, and after removal of the seal, permit liquid to pass the barrier from the upstream portion to the downstream portion. As such, the device can retain liquid in the upstream portion before it is activated, by removal of the seal. The liquid is retained in the upstream portion by the seal preventing liquid flowing past the barrier or back out of the inlet channel. After activation, liquid can pass the barrier to flow into the downstream portion.

Optionally a bridge is provided adjacent the barrier, wherein after removal of the seal the bridge facilitates liquid to flow from the upstream portion to the downstream portion via or over the barrier.

Optionally, the seal is additionally configured to inhibit liquid to flow from the inlet portion to the outlet portion.

Optionally, a surface of the bridge facing the barrier has a wetting contact angle of 90° or less with water, optionally 75° or less. Optionally, the surface of the bridge facing the barrier has a wetting contact angle of 20° or more with water, although the contact angle can be as low as 0°. As such, the surface can be suitably hydrophilic to encourage flow without causing undesirable draining of the sensing chamber an air ingress at the inlet.

Optionally, the surface of the bridge facing the barrier is provided with a chemically hydrophilic layer or treatment, optionally a layer more hydrophilic than the untreated surface of the bridge or a plasma treatment. The surface may be provided with one or more such layers, e.g. a layer of extra material as well as an additional chemical treatment such as a chemical evaporated from a solvent. The surface may also, or independently, comprise a physical texture for increasing the surface area of the surface, optionally pillars, fins and/or grooves provided on the surface.

Optionally, the upstream portion can be filled with liquid between the inlet channel and the outlet channel.

According to another aspect, there is provided a microfluidic device comprising one or more of: a sensor provided in a sensing chamber; a sensing chamber inlet channel and a sensing chamber outlet channel, each connecting to the sensing chamber for respectively passing liquid into and out of the sensing chamber, and a reservoir forming a sample input port to the microfluidic device, the reservoir being in fluid communication with the sensing chamber inlet channel; a liquid collection channel; a barrier between an end of the sensing chamber outlet channel and the liquid collection channel; a first seal, covering the sample input port; a second seal, covering the end of the sensing chamber outlet channel, thereby preventing liquid from flowing from the sensing chamber, over the barrier, into the liquid collection channel; wherein the microfluidic device is filled with a liquid from the first seal at the sample input port to the second seal at the end of the sensing chamber outlet channel, such that the sensor is covered by liquid and unexposed to a gas or gas/liquid interface; and wherein the first and second seals are removable to cause the liquid between the reservoir and the end of the sensing chamber outlet channel to flow so that some liquid flows over the barrier. Such a device reliably keeps the sensor in a state (the 'inactive') state that protects the sensor before the seals are removed, yet is simple for the user to activate into an 'active' state by removing the seals so that device can be used for its sensing purpose.

The outlet channel can have a first end connected to the sensing chamber and a second end which can be covered by the second seal. The barrier can be between the second end of the sensing chamber outlet channel and the liquid collection channel.

Optionally a surface of the barrier cover facing the barrier has a wetting contact angle of 90° or less with water, optionally 75° or less. Optionally, the surface of the barrier cover facing the barrier has a wetting contact angle of 20° or more with water, although the contact angle can be as low as 0°. As such, the surface can be suitably hydrophilic to encourage flow without causing undesirable draining of the sensing chamber an air ingress at the inlet.

The first seal can cover the reservoir.

Optionally, the device is configured such that the removal of the first and second seals does not cause the sensor to become exposed to a gas or gas/liquid interface. This can be achieved by balancing the capillary forces across the device.

Optionally, the first and second seal are connected, such that they can be removed together. Optionally the device further comprises a seal handle attached to the first and second seal, which can be pulled to remove the first and second seals. This allows the device to be activated by one simple, single, action.

Optionally the device further comprises a barrier cover forming a bridging channel over the barrier for connecting the sensing chamber outlet to the liquid collection channel. The barrier cover can be biased towards a position to connect the sensing chamber outlet to the liquid collection channel. The second seal can be positioned under the barrier cover, between the end of the sensing chamber outlet channel and the bridging channel. A release liner can be connected to the second seal, to assist with the removal of the seal. The handle can form part of the release liner. The release liner can be positioned between the second seal and the barrier cover. Accordingly, the barrier cover helps complete the fluidic pathway through the device, in the active state. The provision of the seal and/or release liner between the barrier and the barrier cover provides a convenient and easy to use way of deactivating the device in a way that can be readily reversed by the user to activate the device.

Optionally, the barrier cover further comprises a dipper, extending from the bridging channel towards the sensing chamber outlet channel, for encouraging flow into the bridging channel. The bridging channel can comprise a bend connecting to a downcomer (in the orientation where the bridging channel is arranged above the barrier) beside the barrier, and wherein the bend includes a curved profile on at least one side. The liquid collection channel can comprise a bend between a downcomer beside the barrier and a main portion of the liquid collection channel, and wherein the bend includes a curved profile on at least one side. These features assist with ensuring that flow through the device is not hindered by meniscus pinning during the activation and/or first use of the device.

Optionally the second seal is attached to the surface of the microfluidic device by a glue that is more or less hydrophilic than the surface.

Optionally, the barrier cover is biased to urge contact between the end of the sensing chamber outlet channel and the bridging channel. The barrier cover can have a gasket to seal between the end of the sensing chamber outlet channel and the bridging channel. These features ensure a good seal is provided in the active state.

According to another aspect, there is provided a method of preparing a microfluidic device according to any one of the preceding claims, the method comprising removing the first and second seals, thereby causing liquid between the reservoir and the end of the sensing chamber outlet to flow so that some liquid flows over the barrier to activate the device.

BRIEF DESCRIPTION OF THE DRAWINGS

The invention is described below with reference to exemplary Figures, in which:

FIG. 4b shows a schematic cross-section along the flow path through the device of FIG. 4a;

DETAILED DESCRIPTION OF EXEMPLARY EMBODIMENTS

The present disclosure allows for a microfluidic device, using a "wet-sensor" (i.e. a sensor that functions in a wet environment) to be produced and stored in a state in which the sensor is kept wet, until it is needed. This is effectively achieved by providing a device that has an "inactive" state in which the sensor is kept wet, but in which the device cannot be used, and an "active" state in which the device can be used. In other words, an "inactive" state can be a state in which a flow path between a sample input port and a liquid collection channel is not complete, as discussed below. In contrast an "active" state, can be a state in which the flow path between a sample input port and a liquid collection channel is complete. A particular benefit of keeping the sensor wet when considering nanopore sensors (see more detail below) is to ensure that well liquid does not escape through the membrane. The membrane is very thin and the sensor is very sensitive to moisture loss. Moisture loss can create for example a resistive air gap between the well liquid and the membrane thus breaking the electrical circuit between an electrode provided in the well and in the sample. Moisture loss can also serve to increase the ionic strength of the well liquid, which could affect the potential difference across the nanopore. The potential difference has an effect on the measured signal and thus any change would have an effect on the measurement values.

In any case the device of the invention can be maintained in the "inactive" state for a long period of time until it is required. During that time, for example, the device could be transported (e.g. shipped from a supplier to an end user), as the "inactive" state is robust and capable of maintaining the sensor in a wet condition, even when the device is in a non-standard orientation (i.e. orientations in which the device is not used to perform its normal function). This is possible because the inactive states seals an internal volume of the device, containing the sensor, from the surroundings. That internal volume (referred to as a 'saturated volume' below) is filled with liquid. The absence of any air gaps and/or bubbles means the sensor isolated from the possibility of a gas/air interface intersecting with the sensor (which could damage the functionality of the sensor) even if the device is moved around. Further, even in the active state, the device is able to maintain the sensor in a wet condition, for a long period of time, even if the device is activated and then not used.

Figure 2:
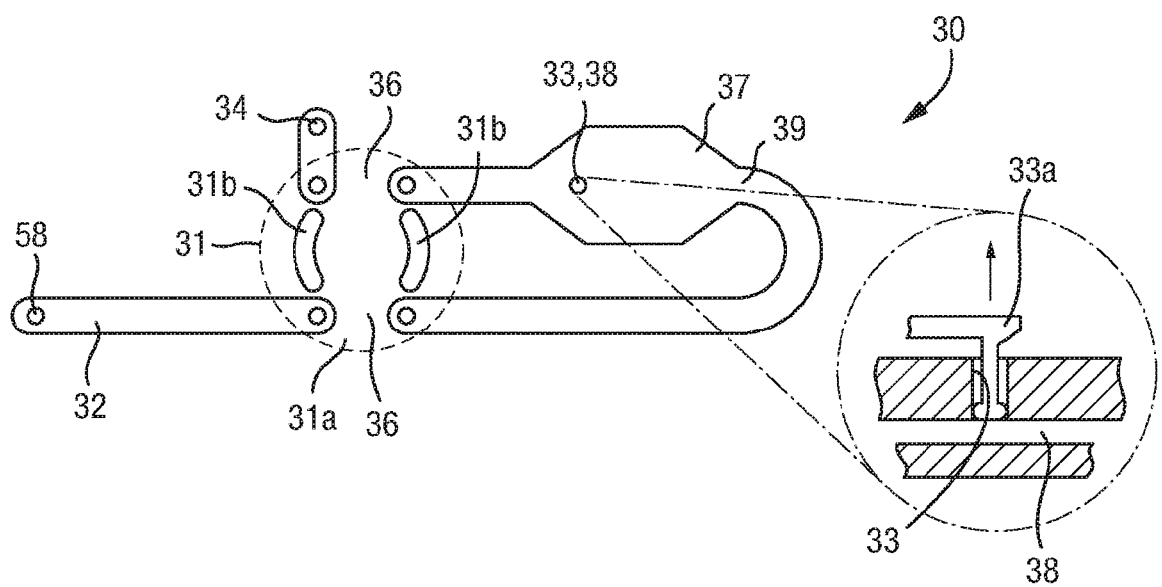
FIG. 2 shows an example of a microfluidic device.

FIG. 2 shows a top cross-sectional view of an example of a microfluidic device 30 with an inset showing a side cross-sectional view of a portion of the microfluidic device comprising a sample input port 33. The microfluidic device 30 comprises a sensing chamber 37, for housing a sensor.

Figure 1:
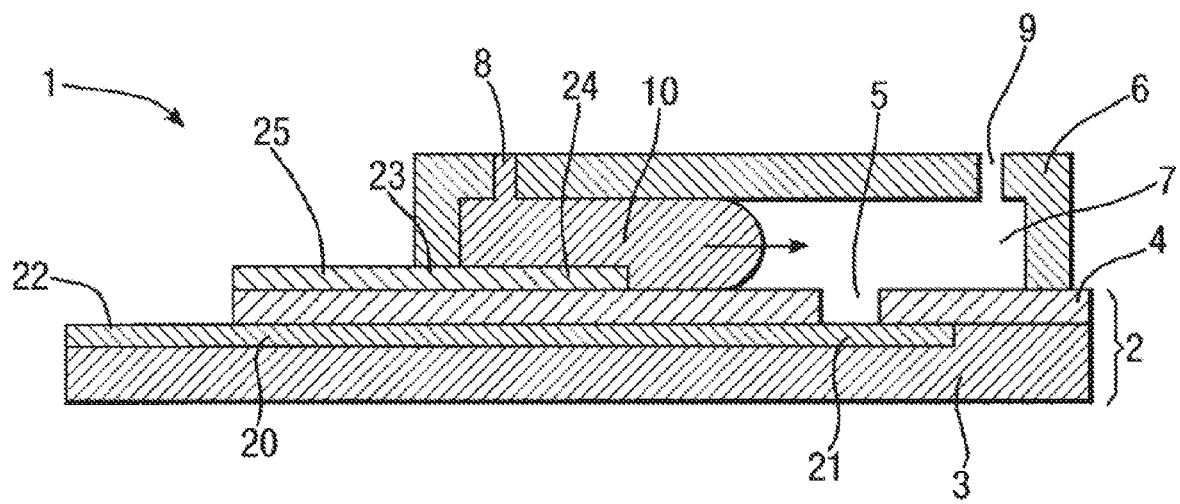
FIG. 1 shows an prior art apparatus which may be used to form a layer of amphiphilic molecules.

The sensing chamber 37 is provided with a sensor, which is not shown in FIG. 2. The sensor may be a component or device for analysing a liquid sample. For example, a sensor may be a component or device for detecting single molecules (e.g., biological and/or chemical analytes such as ions, glucose) present in a liquid sample. Different types of sensors for detecting biological and/or chemical analytes such as proteins, peptides, nucleic acids (e.g., RNA and DNA), and/or chemical molecules are known in the art and can be used in the sensing chamber. In some embodiments, a sensor comprises a membrane that is configured to permit ion flow from one side of the membrane to another side of the membrane. For example, the membrane can comprise a nanopore, e.g., a protein nanopore or solid-state nanopore. In some embodiments, the sensor may be of the type discussed with reference to FIG. 1, above, which is described in WO 2009/077734, the content of which is incorporated herein by reference The sensor is connected to an electrical circuit, in use. The sensor may be an ion selective membrane provide directly over an electrode surface or over a ionic solution provided in contact with an underlying electrode.

The sensor may comprise an electrode pair. One of more of the electrodes may be functionalised in order to detect an analyte. One or more of the electrodes may be coated with a selectively permeable membrane such as NafionTM.

Figure 3:
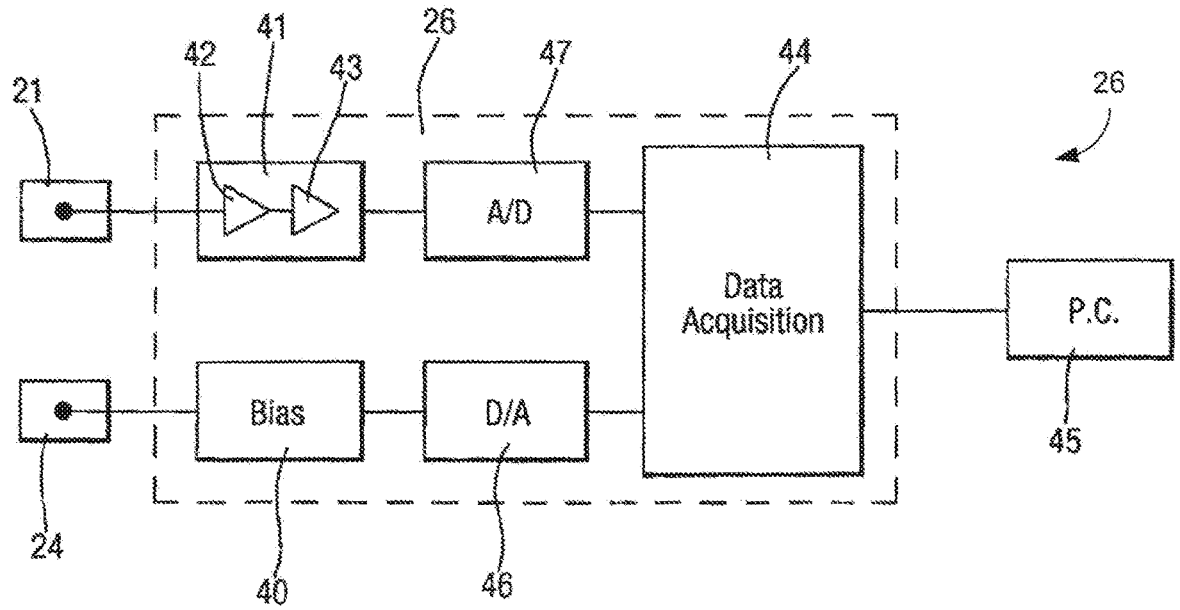
FIG. 3 shows an example design of an electrical circuit.

An example design of such an electrical circuit 26 is shown in FIG. 3. The primary function of the electrical circuit 26 is to measure the electrical signal (e.g., current signal) developed between the common electrode first body and an electrode of the electrode array. This may be simply an output of the measured signal, but in principle could also involve further analysis of the signal. The electrical circuit 26 needs to be sufficiently sensitive to detect and analyse currents which are typically very low. By way of example, an open membrane protein nanopore might typically pass current of 100 pA to 200 pA with a 1M salt solution. The chosen ionic concentration may vary and may be between for example 10 mM and 2M. Generally speaking the higher the ionic concentration the higher the current flow under a potential or chemical gradient. The magnitude of the potential difference applied across the membrane will also effect the current flow across the membrane and may be typically chosen to be a value between 50 mV and 2V, more typically between 100 mV and 1V.

In this implementation, the electrode 24 is used as the array electrode and the electrode 21 is used as the common electrode. Thus the electrical circuit 26 provides the electrode 24 with a bias voltage potential relative to the electrode 21 which is itself at virtual ground potential and supplies the current signal to the electrical circuit 26.

The electrical circuit 26 has a bias circuit 40 connected to the electrode 24 and arranged to apply a bias voltage which effectively appears across the two electrodes 21 and 24.

The electrical circuit 26 also has an amplifier circuit 41 connected to the electrode 21 for amplifying the electrical current signal appearing across the two electrodes 21 and 24. Typically, the amplifier circuit 41 consists of a two amplifier stages 42 and 43.

The input amplifier stage 42 connected to the electrode 21 converts the current signal into a voltage signal.

The input amplifier stage 42 may comprise a transimpedance amplifier, such as an electrometer operational amplifier configured as an inverting amplifier with a high impedance feedback resistor, of for example 500MΩ, to provide the gain necessary to amplify the current signal which typically has a magnitude of the order of tens to hundreds of pA.

Alternatively, the input amplifier stage 42 may comprise a switched integrator amplifier. This is preferred for very small signals as the feedback element is a capacitor and virtually noiseless. In addition, a switched integrator amplifier has wider bandwidth capability. However, the integrator does have a dead time due to the necessity to reset the integrator before output saturation occurs. This dead time may be reduced to around a microsecond so is not of much consequence if the sampling rate required is much higher. A transimpedance amplifier is simpler if the bandwidth required is smaller. Generally, the switched integrator amplifier output is sampled at the end of each sampling period followed by a reset pulse. Additional techniques can be used to sample the start of integration eliminating small errors in the system.

The second amplifier stage 43 amplifies and filters the voltage signal output by the first amplifier stage 42. The second amplifier stage 43 provides sufficient gain to raise the signal to a sufficient level for processing in a data acquisition unit 44. For example with a 500MΩ feedback resistance in the first amplifier stage 42, the input voltage to the second amplifier stage 43, given a typical current signal of the order of 100 pA, will be of the order of 50 mV, and in this case the second amplifier stage 43 must provide a gain of 50 to raise the 50 mV signal range to 2.5V.

The electrical circuit 26 includes a data acquisition unit 44 which may be a microprocessor running an appropriate program or may include dedicated hardware (e.g., personal computer (P.C.) 45). In this case, the bias circuit 40 is simply formed by an inverting amplifier supplied with a signal from a digital-to-analogue converter 46 which may be either a dedicated device or a part of the data acquisition unit 44 and which provides a voltage output dependent on the code loaded into the data acquisition unit 44 from software. Similarly, the signals from the amplifier circuit 41 are supplied to the data acquisition card 40 through an analogue-to-digital converter 47.

The various components of the electrical circuit 26 may be formed by separate components or any of the components may be integrated into a common semiconductor chip. The components of the electrical circuit 26 may be formed by components arranged on a printed circuit board. In order to process multiple signals from the array of electrodes the electrical circuit 26 is modified essentially by replicating the amplifier circuit 41 and A/D converter 47 for each electrode 21 to allow acquisition of signals from each recess 5 in parallel. In the case that the input amplifier stage 42 comprises switched integrators then those would require a digital control system to handle the sample-and-hold signal and reset integrator signals. The digital control system is most conveniently configured on a field-programmable-gate-array device (FPGA). In addition the FPGA can incorporate processor-like functions and logic required to interface with standard communication protocols i.e. USB and Ethernet. Due to the fact that the electrode 21 is held at ground, it is practical to provide it as common to the array of electrodes.

In such a system, polymers such as polynucleotides or nucleic acids, polypeptides such as a protein, polysaccharides or any other polymers (natural or synthetic) may be passed through a suitably sized nanopore. In the case of a polynucleotide or nucleic acid, the polymer unit may be nucleotides. As such, molecules pass through a nanopore, whilst the electrical properties across the nanopore are monitored and a signal, characteristic of the particular polymer units passing through the nanopore, is obtained. The signal can thus be used to identify the sequence of polymer units in the polymer molecule or determine a sequence characteristic. A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov AP et al., Nano Lett. 2011 Jan. 12; 11(1):279-85), and FET measurements (International Application WO 2005/124888). Optical measurements may be combined with electrical measurements (Soni GV et al., Rev Sci Instrum. 2010 January; 81(1):014301). The measurement may be a transmembrane current measurement such as measurement of ionic current flowing through the pore.

The polymer may be a polynucleotide (or nucleic acid), a polypeptide such as a protein, a polysaccharide, or any other polymer. The polymer may be natural or synthetic. The polymer units may be nucleotides. The nucleotides may be of different types that include different nucleobases.

The nanopore may be a transmembrane protein pore, selected for example from MspA, lysenin, alpha-hemolysin, CsgG or variants or mutations thereof.

The polynucleotide may be deoxyribonucleic acid (DNA), ribonucleic acid (RNA), cDNA or a synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The polynucleotide may be single-stranded, be double-stranded or comprise both single-stranded and double-stranded regions. Typically cDNA, RNA, GNA, TNA or LNA are single stranded.

In some embodiments, the devices and/or methods described herein may be used to identify any nucleotide. The nucleotide can be naturally occurring or artificial. A nucleotide typically contains a nucleobase (which may be shortened herein to "base"), a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

The nucleotide can include a damaged or epigenetic base. The nucleotide can be labelled or modified to act as a marker with a distinct signal. This technique can be used to identify the absence of a base, for example, an abasic unit or spacer in the polynucleotide. Of particular use when considering measurements of modified or damaged DNA (or similar systems) are the methods where complementary data are considered. The additional information provided allows distinction between a larger number of underlying states.

The polymer may also be a type of polymer other than a polynucleotide, some non-limiting examples of which are as follows.

The polymer may be a polypeptide, in which case the polymer units may be amino acids that are naturally occurring or synthetic.

The polymer may be a polysaccharide, in which case the polymer units may be monosaccharides.

A conditioning liquid provided in the device to maintain the sensor in a wet state may be any liquid that is compatible with the device (e.g., a liquid that does not adversely affect the performance of the sensor) By way of example only, when the sensor comprise a protein nanopore, it would be apparent to one of ordinary skill in the art that the conditioning liquid should be free of an agent that denatures or inactivates proteins. The conditioning liquid may for example comprise a buffer liquid, e.g., an ionic liquid or ionic solution. The conditioning liquid may contain a buffering agent to maintain the pH of the solution.

The sensor is one that needs to be maintained in a 'wet condition', namely one which is covered by a liquid. The sensor may comprise a membrane, such as for example an ion selective membrane or amphiphilic membrane. The membrane, which may be amphiphilic, may comprise an ion channel such as a nanopore.

The membrane, which may be amphiphilic, may be a lipid bilayer or a synthetic layer. The synthetic layer may be a diblock or triblock copolymer.

The membrane may comprise an ion channel, such an ion selective channel, for the detection of anions and cations. The ion channel may be selected from known ionophores such as valinomycin, gramicidin and 14 crown 4 derivatives.

Returning to FIG. 2, the sensing chamber has a liquid inlet 38, and a liquid outlet 39, for respectively passing liquid into and out of the sensing chamber 37. In the inset of FIG. 2, it is shown, in cross section through the device 30, that the inlet 38 is in fluid communication with a sample input port 33. The sample input port 33 is configured for introducing, e.g. delivering, a sample to the microfluidic device 30, e.g. for testing or sensing. A seal 33A, such as a plug, may be provided to seal or close the sample input port 33, when the device 30 is in its inactive state, to avoid any fluid ingress or egress through the sample input port 33. As such, the seal 33A may be provided within the sample input port 33 in the inactive state. Preferably the seal 33A is removable and replaceable. The sample input port may be desirably situated close to the sensing chamber, such as shown in FIG. 2, wherein the port is provided directly at the sensing chamber. This reduces the volume of sample liquid that needs to be applied to the device by reducing the volume of the flow path.

Downstream from the outlet 39 of the sensing chamber 37 is a liquid collection channel 32. The liquid collection channel can be a waste collection reservoir, and is for receiving fluid that has been expelled from the sensing chamber 37. At the most downstream end, e.g. the end portion, of the collection channel 32 is a breather port 58, for allowing gas to be expelled as the collection channel 32 receives liquid from the sensing chamber and fills with the liquid.

In the example shown in FIG. 2, upstream of the sensing chamber 37, is a liquid supply port 34, which is optional. This port provides the opportunity to supply liquid, for example a buffer, into the device, once the device 30 is in its active state. It can also be used for delivering larger volume samples, if desired, and for high volume flushing/perfusion of previous samples from the sensing chamber 37 before a new sample is delivered.

As described below in more, the device is configured to accept a sample at the sample input port, which is subsequently drawn into the sensing chamber of its own accord, without the aid of an external force or pressure, e.g. by capillary pressure as described below. This removes the need for the user to introduce a test liquid into the device under an applied positive pressure.

In FIG. 2, the device 30 is in an inactive state. This is achieved by the provision of a valve 31 which is configured in a close state, which is a state that does not permit fluid flow between the liquid collection channel 32 and the sensing chamber 37, as well as the provision of the seal 33A on the sample input port 33, which seals or closes the sample input port 33. In the inactive state, as shown in FIG. 2, flow through the sensing chamber 37 is not possible. The valve 31 in a closed state is a structure that serves as a flow path interruption between the liquid outlet 39 of the sensing chamber 37 and the liquid collection channel 32, preventing upstream liquid (e.g., liquid from the sensing chamber 37) from flowing into the liquid collection channel 32. Similarly, the valve 31 in a closed state is a structure that serves as a flow path interruption between the supply port 34 and the sensing chamber 37, preventing upstream liquid (e.g., liquid introduced through the supply port) from flowing into the sensing chamber 37. As such, the sensing chamber 37 is isolated from the supply port 34 and the waste collection reservoir, in the form of liquid collection channel 32 (which may be open to the atmosphere). Further, the provision of the plug 33A sealing the sample input port 33 ensures that the sensing chamber 37 is entirely isolated. The plug 33A can also serve an additional purpose: when it is removed it can created a 'suction' in the inlet 38, ensuring that the port 33 becomes wetted (and hence ready to receive sample fluid) as the plug 33A is removed. As such, the plug 33A provides a priming action. The priming action can draw fluid from the liquid collection channel (e.g., indirectly, displacing fluid into the sensing chamber 37, which in turn is displaced into the inlet 38 and the port 33) or a separate priming reservoir (see examples below).

In some embodiments, the valve 31 serves a dual function. For example, as shown in FIG. 2, the valve 31 can be configured in a state such that it acts an activation system. An activation system can complete the flow path between the liquid outlet 39 and the liquid collection channel 32 (and also the flow path between the supply port 34 and the sensing chamber 37). Further, as discussed in more detail below, such activation occurs without draining the sensor chamber 37 of liquid. That is, the sensing chamber 37 remains unexposed to gas or a gas/liquid interface after activation. In the example of FIG. 2, this is achieved by rotation of the valve 31 by 90° (from the depicted orientation) within the valve seat 31A. This leads to channels 31B of the valve completing flow path interruptions 36 between the liquid outlet 39 and the liquid collection channel 32, as well as between the buffer liquid input port 34 and the sensing chamber 37. In that active state, it is possible for liquid to flow from the buffer supply port 34 (also referred to herein as a 'purge port') through the sensing chamber 37 and into the liquid collection channel 32. However such flow does not occur freely, as discussed in more detail in connections with FIGS. 5*a-f*, below.

As a result, the sensing chamber 37 can be pre-filled with a conditioning liquid, such as a buffer, before turning the valve 31 into the position shown in FIG. 2. It should be noted that the type of the conditioning liquid is not particularly limited according to the invention, but should be suitable according to the nature of the sensor 35. Assuming the plug 33A has been inserted and that the sensor chamber 37 is appropriately filled so that there are no air bubbles, there is then no opportunity for the sensor to come into contact with a gas/liquid interface which would potentially be damaging to the sensor. As such, the device 30 can be robustly handled, without fear of damaging the sensor itself.

Figure 4A:
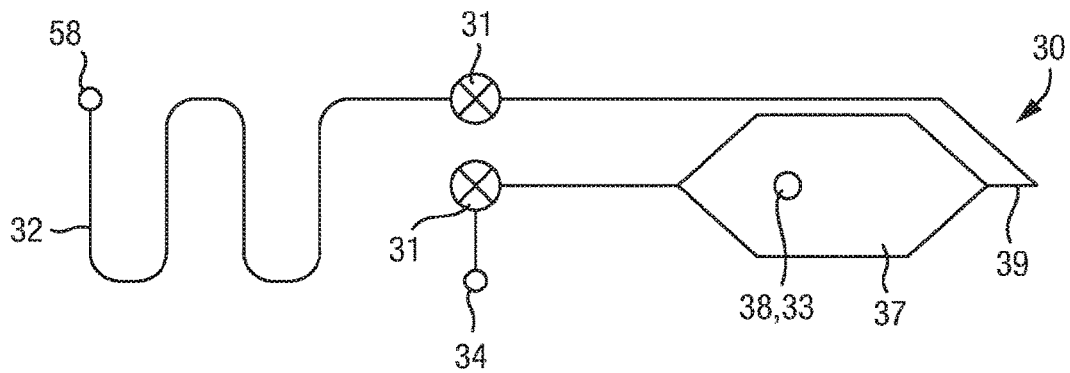
FIG. 4a shows a schematic of a device corresponding to that of FIG. 2.

FIG. 4*a* shows a schematic of a device 30 corresponding to that of FIG. 2. In FIG. 4, the fluid channels are simply shown as lines. Further, the valve 31 is shown as two separate valves 31 upstream and downstream of the sensing chamber 37. This is for the sake of clarity, but in some embodiments it may be desirable to have two separate valves 31 as shown.

Figure 4B:
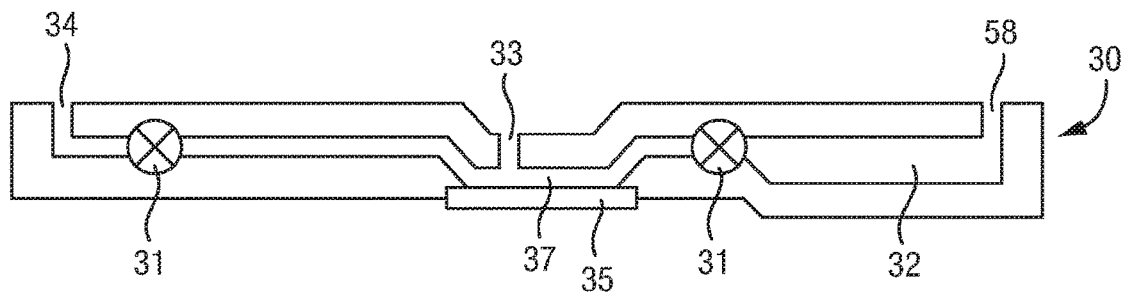

FIG. 4*b* shows a schematic cross-section along the flow path through the device of FIG. 4*a*. This may not be a 'real' cross-section, in the sense that the flow path may not be linear in the way depicted in FIG. 4*b*. Nonetheless, the schematic is useful in understanding the flow paths available to the liquid in the device 30. In particular, the upstream buffer supply/purge port 34 can be seen to be separated from the sensing chamber by upstream valve 31. Further downstream breather port 58 can be seen to be separated from the sensing chamber 37 by downstream valve 31. As such, it becomes readily apparent that the sensing chamber 37 may be filled with fluid and isolated from the upstream and downstream ports 34 and 58. Further, by providing a seal over sample input port 33, the sensing chamber can be entirely isolated.

It is also instructive to consider the scale of the features presented in FIGS. 4a and 4b.

The purge port 34 and the sample input port 33 may be of similar design, as both are configured to receive a fluid to be delivered to the device 30. In some embodiments, the ports 33 and/or 34 may be designed to accommodate the use of a liquid delivery device, e.g., a pipette tip, to introduce liquid into the ports. In preferred embodiments, both ports have a diameter of around 0.4 to 0.7 mm, which allows for wicking of fluid into the ports whilst also limiting the possibility of the device 30 free-draining of liquid (discussed in more detail below). In contrast the size of the downstream breather port 58 is less important, as it is not intended, in routine use, for accepting liquid delivery devices (e.g., pipettes) or delivering liquid.

The size of the sensor any vary and depend upon the type and the number of sensing elements, for example nanopores or ion selective electrodes, provided in the sensor. The size of the sensor 35 may be around 8×15 mm. As discussed above, it can be an array of sensing channels, with a microscopic surface geometry that contains membranes with nanopores.

The 'saturated volume' of the device 30 is the volume, e.g. the flow path volume, connecting between the valves 31 (one valve controls flow between the liquid outlet 39 and the liquid collection channel 32, and another valve controls flow between the buffer liquid input port 34 and the sensing chamber 37) that can be filled with liquid and sealed and isolated from the surroundings when the plug 33a is present, i.e. to seal the simple input port 33, and valves 31 are configured in a closed state. In one embodiment, the saturated volume can be around 200 µl, which can vary depending on the design of the flow path in the devices described herein. However, smaller volumes are more preferable (to reduce the size of sample required, for example) and preferably the saturated volume is 20 µl or less. In other configurations, the provision of the purge port 34 (and connecting fluid path to the sensing chamber 37) may not be necessary, in which case the saturated volume will extend from the sealed sample input port 33 to the sensing chamber 37 and past the liquid outlet 39 to the flow path interruption 36.

In contrast it is desirable for the liquid collection channel 32 to have a much larger volume, e.g., a volume that is at least 3-fold larger, e.g., at least 4-fold larger, at least 5-fold larger, at least 10-fold larger, or at least 15-fold larger, than the saturated volume, so it can collect liquid expelled from the saturated volume over several cycles of testing and flushing. In one embodiment, the liquid collection channel 32 may have a volume of 2000 µl. The hydraulic radius of the liquid collection channel is typically 4 mm or less.

The sizes of the valves 31 are not particularly important (and, as discussed below, alternative flow channel interruptions can be provided). They serve the function of isolating the saturated volume in connection with the plug 33a.

Further, even in the active state, the device is resistant to the sensing chamber 37 drying out. This is discussed below, with reference to FIG. 5a, which is a schematic cross-section of the sensing chamber 37 according to one embodiment and surrounding connections of the device 30 of FIG. 2 or FIG. 4, for example.

Figure 5A:
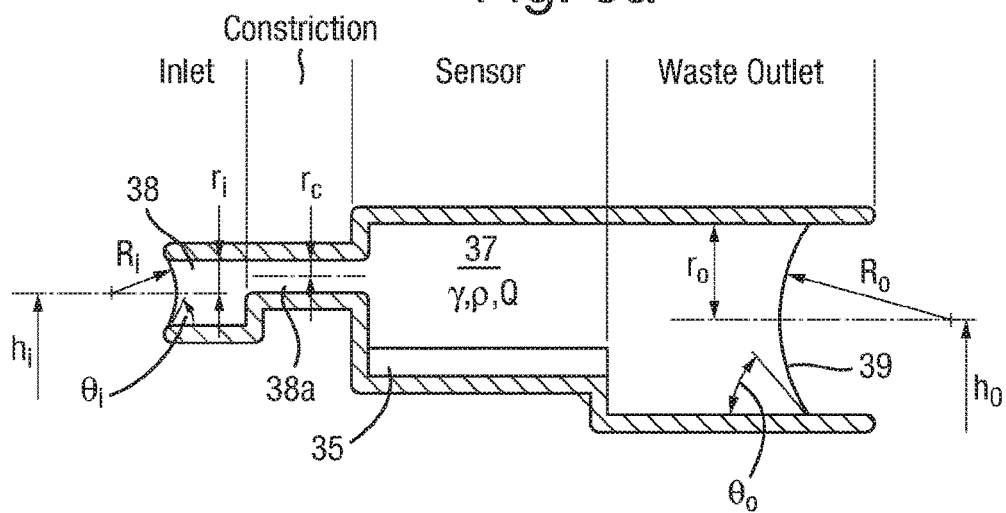
FIG. 5a is a schematic cross-section of a sensing chamber and surrounding connections of the device of FIG. 2 or FIG. 4, for example.

In FIG. 5a, the sensor 35 is provided in a sensing chamber 37. The sensing chamber liquid inlet 38 is connected upstream of the sensing chamber 37, for simplicity of presentation (i.e. although the liquid inlet 38 is shown as entering sensing chamber 37 from above in FIGS. 2 and 4, the change in location in FIG. 5a does not affect the outcome of the analysis below). FIG. 5a shows a further restriction 38a in the diameter of the liquid inlet before it reaches the sensing chamber 37. This could be for example, due to a widening of the input 33 to ease sample collection/provision. Downstream of the sensing chamber 37 is the liquid outlet 39 to the liquid collection channel 32.

In the diagram, several parameters and dimensions are indicated. Heights (measured in metres) are indicated by the symbol h. Radii of curvature (measured in metres) are indicated by the symbol R. Radii of the tubular parts (measured in metres) are indicated by the symbol r. Surface tension (measured in N/m) is indicated by the symbol γ. Liquid density (measured in kg/m$^3$) is indicated by the symbol ρ. Flow rates (measured in m$^3$/s) is indicated by the symbol Q. Contact angles (measured in degrees) of liquid/gas meniscii with the device 30 walls, are indicated by the symbol θ. The subscripts "i" are used to refer to conditions at the inlet, the subscript "c" is used to indicate conditions at the constriction, and the subscript "o" is used to indicate conditions at the outlet.

The behaviour of fluid in the depicted system is controlled by capillary and/or Laplace bubble pressures and Poiseuille pressure drops to limit flow rates. As is generally known, capillary pressure at a meniscus can be calculated using the equation:

$$P_c = \gamma\left(\frac{1}{R_1} + \frac{1}{R_2}\right) \qquad \text{Equation 1}$$

where $R_1$ and $R_2$ are radii of curvature in perpendicular directions. In the case of a tube, such as a capillary, the radius of curvature $R_1$ is the same as the radius of curvature $R_2$ and the radius of curvature is related to the radius of the tube by the following equation:

$$E = \frac{r}{\cos\theta} \qquad \text{Equation 2}$$

Further, in a rectangular channel, where $R_1$ is not the same as $R_2$, the radii of curvature are given by the following equations:

$$R_1 = \frac{a/2}{\cos\theta}; \quad R_2 = \frac{b/2}{\cos\theta} \qquad \text{Equations 3}$$

where a is e.g. the width of the rectangular section, and b is the height of the rectangular section.

For incompressible Newtonian fluids, assuming un-accelerated lamina flow in a pipe of constant circular cross-section that is substantially longer than its diameter, the pressure losses can be calculated from the Hagen-Poiseuille equation:

$$P_{FR} = \frac{8 \mu l Q}{\pi r^4} \quad \text{Equation 4}$$

where μ is the viscosity (measured in N.s/m²) of the liquid, l is the length of the tube through which flow occurs (in metres) and r is the radius of the tube (in metres).

Finally, static pressure is calculated according to the following equation:

Equation 5

$$P_h = \rho g h$$

in which g is the acceleration due to gravity (9.81 m/s²), and h is the height of the fluid column.

Figure 5B:
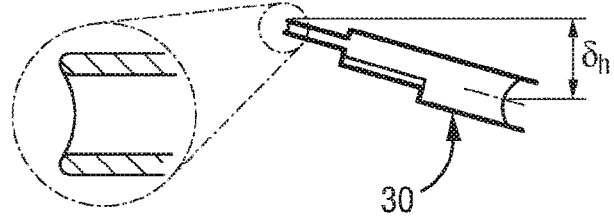
FIG. 5b illustrates a scenario in which an activated device is tilted to encourage fluid in the device to drain into the waste collection channel.

FIG. 5b illustrates a scenario in which an activated device 30 is tilted to encourage fluid in the device 30 to drain into the liquid collection channel 32. When considering whether fluid will remain at the opening to the inlet 38 (i.e. the sample input port 33), it can be understood that the capillary pressure at the inlet ($P_{ci}$) must be equal to or greater than the capillary pressure at the outlet plus any difference in hydrostatic pressure brought about by the inlet not being at the same height as the outlet (that difference in height being denoted as δh in FIG. 5b and the equations below) to avoid free draining. This is set out in the following equation:

$$P_{ci} \geq P_{co} + \rho g \cdot \delta h$$

From this equation, in combination with equations 1 and 2, the maximum height difference dh before free draining occurs can be deduced (assuming the same contact angle θ at the inlet and the outlet):

$$\frac{2\gamma\cos\theta}{r_1} = \frac{2r\cos\theta}{r_0} + \rho g \cdot \delta h$$

$$\delta h = \frac{\frac{2\gamma\cos\theta}{r_1} - \frac{2r\cos\theta}{r_0}}{\rho g}$$

$$\delta h = \left(\frac{1}{r_1} - \frac{1}{r_0}\right)\frac{2\gamma\cos\theta}{\rho g}$$

Substituting typical values of the relevant variables (e.g. $r_1$=0.4 mm, $r_0$=3.0 mm, θ=82°, p=1000 kg/m³, γ=0.072 N/m), indicates that a difference in height of about 4 mm can be achieved before the inlet de-wets.

Figure 5C:
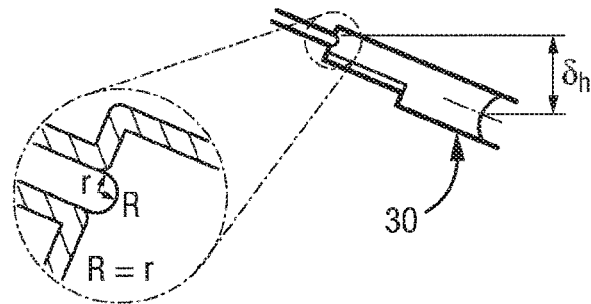
FIG. 5c shows a difference in height between an inlet and an outlet.

Considering this further, and as shown in FIG. 5c, if the difference in height exceeds this critical value, the meniscus at the input port 33 will retreat to the inlet to the sensing chamber. In the limit before the meniscus detaches from that inlet (i.e. allowing gas into the sensing chamber 37), the meniscus will have the maximum radius of curvature, being equal to the radius of the inlet (ignoring any constriction 38a). In that case, the contact angle θ will be zero and so the non-draining scenario is described by:

$$P_{ci} \geq P_h + P_{co}$$

and in the limit:

$$\frac{2\gamma\cos\theta_1}{r_1} = \rho g \cdot \delta h + \frac{2\gamma\cos\theta_0}{r_0}$$

$$\delta h = \frac{\frac{2\gamma}{r_1} - \frac{2\gamma\cos\theta_0}{r_0}}{\rho g}$$

$$\delta h = \frac{2\gamma}{\rho g}\left(\frac{1}{r_1} - \frac{\cos\theta_0}{r_0}\right)$$

Again, using the typical values mentioned above, this indicates that the allowable difference in height between the inlet to the sensing chamber and the downstream meniscus and the waste outlet can be of the order of 36 mm. As a result, even if the inlet port 33 itself does not remain wetted, it is unlikely that the sensing chamber 37 will de-wet in normal use, as this is quite a substantial height difference, which would indicate an unusual amount of tilting.

Figure 5D:
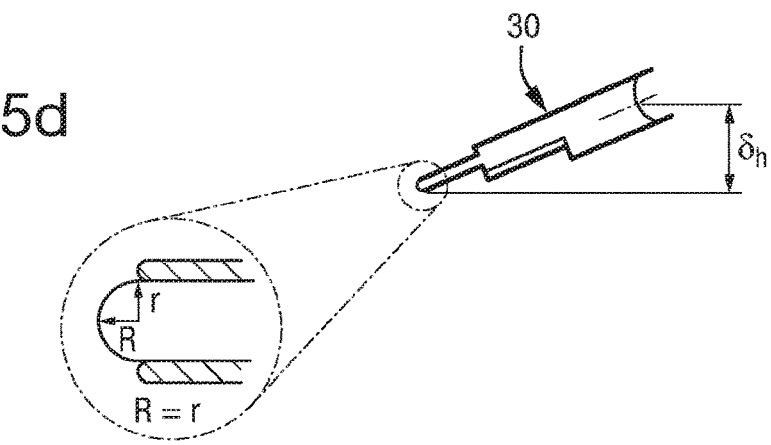
FIGS. 5d-5f show scenarios for the sensing chamber.

Further, it is unlikely that the sensing chamber will de-wet by dripping out of the inlet. As shown in FIG. 5d, the other extreme to the scenario previously considered is the limit before the liquid starts to drip from the inlet. Again, in this case, the radius of curvature of the meniscus (this time in the other direction) to equal the radius of curvature of the inlet capillary itself. In this case, assuming that dh is the difference in height between the inlet meniscus and the outlet meniscus, and that the outlet is raised to encourage flow out of the inlet, the non-drip scenario is described by:

$$P_{ci} \geq P_h - P_{co}$$

and in the limit:

$$\frac{2\gamma\cos\theta_1}{r_1} = \rho g \cdot \delta h + \frac{2\gamma\cos\theta_0}{r_0}$$

$$\delta h = \frac{\frac{2\gamma}{r_1} + \frac{2\gamma\cos\theta_0}{r_0}}{\rho g}$$

$$\delta h = \frac{2\gamma}{\rho g}\left(\frac{1}{r_1} + \frac{\cos\theta_0}{r_0}\right)$$

Once again, substituting typical values indicates that the maximum allowable δh is of the order of 37 mm. Once again, this is well within a tolerable range for normal handling in use.

Therefore, from the above analysis, it can be seen that once the device 30 is switched from an inactive state to an active state, the liquid sensor 35 will remain wetted, in normal conditions. Further, even if the input port 33 becomes de-wetted, this will not necessarily result in the sensor being exposed to a gas/liquid interface, because the interface is likely to be pinned at the entrance to the sensing chamber 37.

Figure 5E:
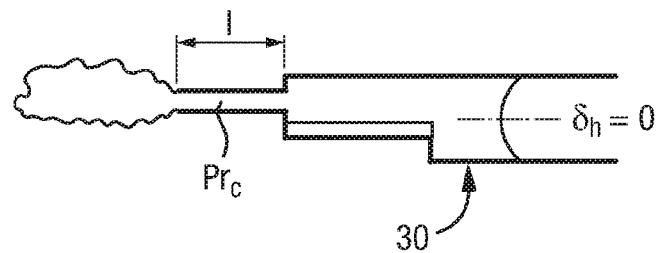

It is also possible to consider how this stability affects the ability to deliver sample to the sensing chamber 37. In FIG. 5e a first extreme of wicking a fluid from a 'puddle' into the input port 33 is considered. In that case, the capillary pressure acting to drawn the fluid in is balanced by the laminar flow losses in the inlet (having length l):

$$P_{co} = \frac{8\mu l\, Q}{\pi r_c^4} = \frac{2\gamma\cos\theta}{r_o}$$

$$Q = \frac{2\gamma\cos\theta}{r_0} \cdot \frac{\pi r_c^4}{8\,\mu l}$$

Applying the typical values (including $\mu=8.9\times10^{-4}$ N·s/m$^2$ and l=3 mm), a flowrate of 25 µl/s can be derived. This is more than sufficient when sample volumes are low, such as in microfluidic devices having a total volume of around 200 µl for example.

Figure 5F:
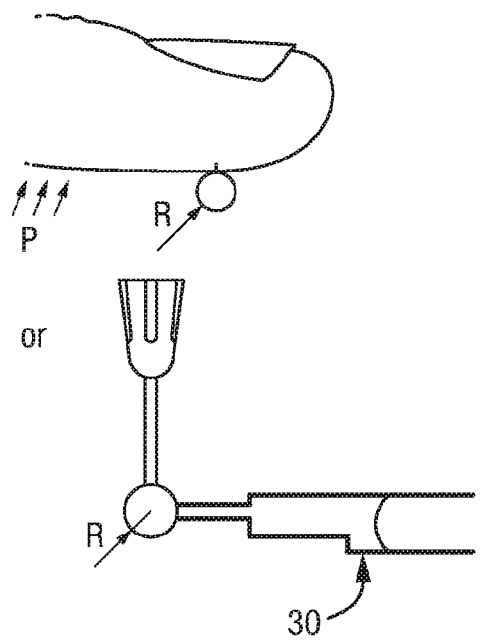

In another extreme, shown in FIG. 5f, the sample may be supplied to the input port 33 as droplet (e.g. a drop of blood from a finger or a droplet from a pipette). In that case, the driving force is the Laplace bubble pressure for the droplet:

$$\Delta P = \frac{2\gamma}{R}$$

For a 1 mm droplet, the pressure is around 144 Pa (using the typical values). A 2D approximation, in comparison to the puddle wicking scenario, indicates that this around 20 times greater, and so a flowrate of around 500 µl/s can be expected for the same viscous drag.

As a result, it can be seen that the device 30, e.g., the dimensions of the inlet 38 and outlet 39 as well as the liquid collection channel 32, can be configured not only to robustly maintain a wetted state in the sensing chamber 37, but may also to operate easily to draw fluid into the sensing chamber 37. When the sample has been supplied, the device 30 returns to a new equilibrium, in which the device will not de-wet/drain dry. That is, the device 30 is configured to avoid free draining of the sensing chamber 37. In particular, the sample input port 33, the sensing chamber inlet 38 and the liquid collection channel 32 are configured to avoid such draining, such that when the activation system has been operated to complete the flow path downstream of the sensing chamber 37, the sensor 35 remains unexposed to gas or a gas/liquid interface even whilst the device 30 is tilted. Put another way, the sensing chamber inlet 33 and the liquid collection channel 32 are thus configured to balance capillary pressures and flow resistances to avoid free draining of the sensing chamber 37 when the flow path is completed.

In considering how the sensing chamber inlet and liquid collection channel are configured to balance capillary pressures and flow resistances, it is helpful to consider the how the device practically functions. Priming of the device into its 'active state' is achieved by completing the flow path between the liquid outlet and the liquid collection channel 32. The capillary pressures at the downstream collection channel and the sample input port are balanced such that following activation of the device, gas is not drawn into the sample inlet port, and the sample input port presents a wet surface to a test liquid. If it were the case that the capillary pressure at the liquid collection channel was greater than at the sample input port, the device would drain following activation, with buffer liquid being drawn into the collection channel.

Following activation of the device and prior to addition of a test liquid, the device may be considered to be at equilibrium, namely wherein the pressure at the input port is equal to the pressure at the downstream collection channel. In this equilibrium state, liquid remains in the sensing chamber and gas is not drawn into the input port such that the input port presents a wet surface to a test liquid to be introduced into the device. The device is configured to ensure that balance of forces are such that the sensing chamber remains filled with liquid and that liquid remains (at least partially) in the inlet, in the outlet and the liquid collection channel. If the equilibrium is disturbed by shifting the position of the liquid (without adding or removing liquid to the system) there is an impetus to return to that equilibrium. When the liquid is moved, it will create new gas/liquid interfaces. Thus this balance of force and restoring of the equilibrium will effectively be controlled by the capillary forces at those interfaces.

Ideally, the balance of force is such that following activation or addition of a volume of liquid, the liquid fills the sample input port and presents a wet surface. However, some adjustment may be necessary following activation/perfusion in order to provide a wet surface at the sample input port. In any case, the inlet port is configured such that following addition of a test liquid to the port, the capillary pressure at the input port is less than the capillary pressure at the downstream collection channel. This provides the driving force to draw test liquid into the device thereby displacing liquid from the sensing chamber into the liquid collection channel. This continues until the pressures at the sample input port and the liquid collection channel once more reach equilibrium. This driving force may be provided by the change in shape of a volume of liquid applied to the input port, as outlined by equation 1, wherein a volume of fluid applied to the port, such as shown in FIG. 5f having a particular radius of curvature, 'collapses' into the port, thus reducing the effective rate of curvature and supplying a Laplace pressure (there may also be other components of the overall driving pressure, e.g. due to the head of pressure of the volume of the test liquid, which will reduce in time as that volume is introduced into the device). The liquid inlet diameter is advantageously less than the diameter of the liquid collection channel such that fluid is located at the input port and over the sensor and that the liquid is present in the device as a continuous phase as opposed to discrete phases separated by gas.

A further volume of sample may be subsequently applied to the device in order to further displace buffer liquid from the sensing chamber. This may be repeated a number of times such that the buffer liquid is removed from the sensor in sensing chamber and replaced by the test liquid. The number of times required to completely displace buffer liquid from the sensor will be determined by the internal volume of the device, the volume of test sample applied as well as the degree of driving force that may be achieved.

Thus in this particular embodiment, a test liquid may be drawn into the device and displace the buffer liquid without the need for the user to apply additional positive pressure, for example by use of a pipette. This has the advantage of simplifying the application of a test liquid to the device. Surprisingly and advantageously, the invention provides a device that may be provided in a 'wet state' wherein liquid may be displaced from the device by the mere application of another liquid to the device.

Figure 6:
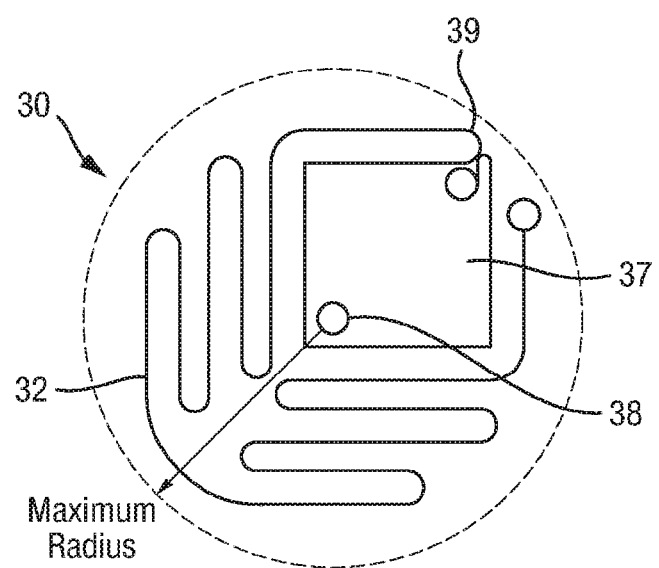
FIG. 6 is a schematic plan of a microfluidic device in an alternative configuration.

Further, the above analysis considers only a linear configuration. FIG. 6 is a schematic plan of an example microfluidic device 30 in an alternative configuration. In this configuration, the waste collection channel 32, downstream of the outlet 39 from the chamber 37 is provided in a twisting or tortuous path, to maintain the channel 32 within a defined maximum radius from the sample input port 38. Such a configuration allows for a large length (and hence volume) of the waste collection channel 32, whilst keeping the maximum distance of the downstream meniscus within the maximum radius. That maximum allowable radius is dictated by the allowable difference in height, between the input port 38 and the downstream meniscus, that does not result in the sensor chamber 37 draining. Put another way, a purely linear arrangement would result in the meniscus reaching the maximum allowable height difference after a certain amount of use, but in the tortuous arrangement the meniscus is diverted back to be closer to the input port 33 and so the critical condition is not reached. That is because the tortuous arrangement maintains the downstream meniscus closer to the input port, a larger angle of tilt is required to obtain the same difference in height (for any given amount of liquid in the downstream channel assuming the dimensions of the channel do not change, only the path of the channel).

Further, even if the sample input port 33 does de-wet, device 30 may be operable so as to re-prime the system in the active state. In the FIGS. 2 and 4 example, additional liquid can be supplied to the inlet 38 directly via the sample input port 33. Alternatively, re-wetting could be encouraged by drawing liquid back through from the outlet 39 and sensing chamber 37 into the inlet 38 and sample input port 33. Another alternative is for additional fluid to be provided via buffer supply port 34.

However, in other embodiments at least the downstream part of valve 31 of the FIG. 2 embodiment might be omitted, and replaced by another form flow path interruption. For example, the downstream waste channel 32 could be isolated from the saturated volume by a surface treatment (e.g. something hydrophobic), which would effectively form a barrier to upstream liquid until the interruption was removed by forced flow initiated by a priming or flushing action. Such a surface treatment would effectively be a hydrophobic valve. In effect, the interruption 36 may be any flow obstacle that may be removed or overcome by an activation system.

Figure 7:
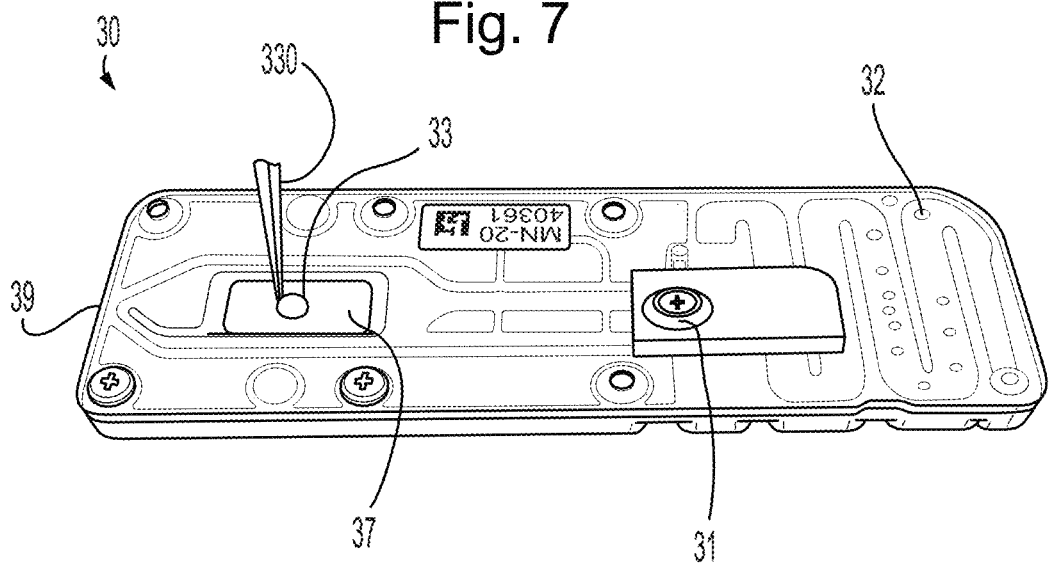
FIGS. 7 and 8 show example embodiments of the present invention.
Figure 8:
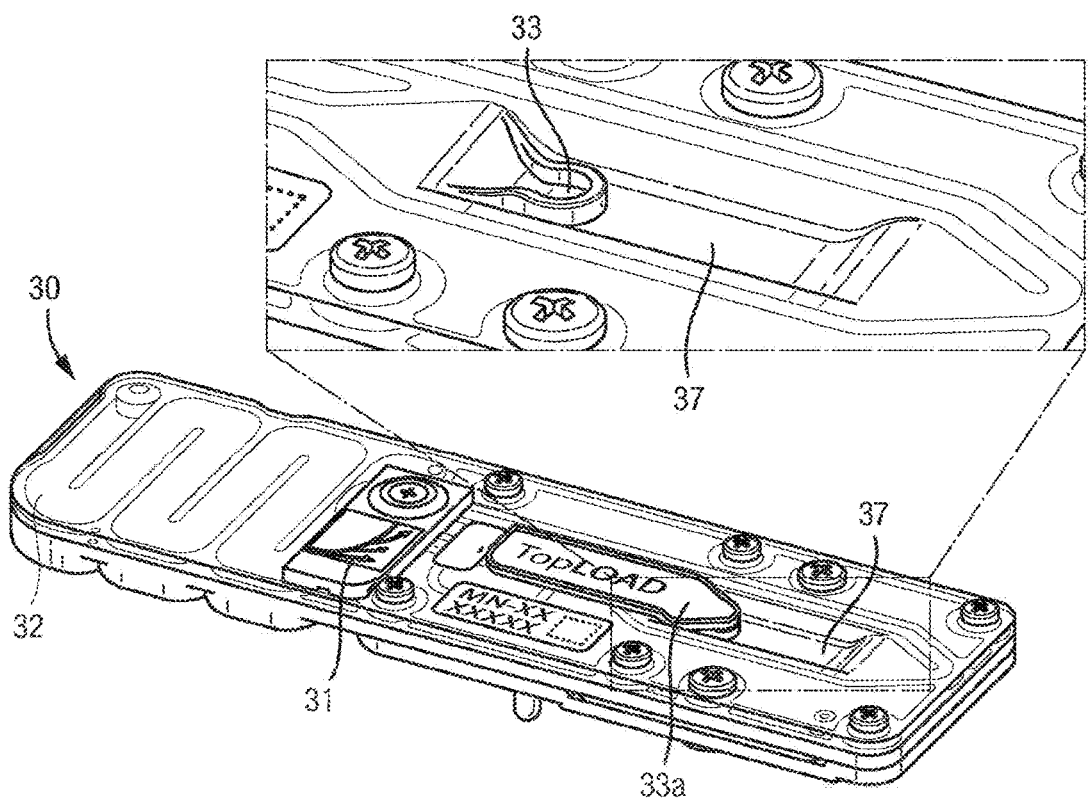

FIGS. 7 and 8 are example embodiments of the devices described herein.

FIG. 7 shows a device 30, in which a pipette 330 is being used to provide sample to the input port 33. The port 33 is provided centrally above the sensor in the sensing chamber 37, in this example. In this example, and the example of FIG. 8, a valve 31 of the type illustrated in FIG. 2 (i.e. a single valve which opens and closes both the upstream and downstream channels to the sample chamber 37) is provided.

In FIG. 8, the main image of the device 30 shows the presence of the plug or seal 33A on the sample input port. The expanded image shows the plug 33A removed, revealing the sample input port 33 below. In this example the sample input port 33 is provided at the most upstream end of the chamber 37 containing the sensor 35. This is advantageous because, in the activated state with the upstream purge port 58 closed, the sample chamber 37 can be filled quickly by forcing sample through port 33, so as to displace buffer liquid already in the sample chamber downstream (i.e. no upstream displacement is possible, due to the closed purge port 58).

Some operating scenarios of the microfluidic device 30 of the present invention (i.e. as exemplified by FIG. 8) are now discussed.

In a first configuration, valve 31 is open, as is sample port 33 (i.e. plug 33A is not present). Purge port/buffer supply port 34 is closed. In this configuration, a pipette may be used at breather port 38 to withdraw all liquid, including from the sample cell. Alternatively, if liquid is supplied to this port, it will displace fluid through the waste reservoir 32 into the sensor chamber 37 and out of the sample port 33.

In another configuration, valve 31 and sample input port 33 are open and breather port 58 is sealed. In this scenario, a pipette can provide fluid into the purge port 34, which will force fluid through the cell, into the sample chamber 37 (i.e. through the saturated volume) and downstream into the reservoir 32. This will also cause the sample input port 33 to wet if it has de-wetted. Alternatively, if the pipette is used to drain liquid, it is possible to drain the sensor chamber and the upstream portion of the device.

In another configuration, the valve 31, the purge port 34 and the breather port 58 are all open. In this configuration, a pipette may be supplied to the sample input port 33 to provide sample into the sensor chamber. Alternatively, if the pipette is applied to drain liquid from the sample input port 33, the sensor chamber 37 can be drained. If this is done slowly, it is also possible to draw liquid back from the waste reservoir 32.

In another scenario, the valve 31 and the purge port 34 are open, whilst the breather port 58 is closed. In this scenario, it is possible to apply fluid via the sample input port 33 to force fluid out of the purge port 34, if required. Alternatively, extracting liquid from the sample input port 33 will draw air into the cell via the purge port.

In another configuration, the valve 31 and the breather port 58 are open, whilst the purge port 34 is closed. In this scenario, a fluid supplied to the sample input port 33 can be pushed into the cell more quickly, without fluid spilling from the purge port. Alternatively, extracting fluid from the sample input port 33 in this scenario will drain the cell and the downstream waste, if done quickly.

In a further two configurations, the valve 31 is closed. In some configurations, closing valve 31 may connect the upstream purge port 34 to the downstream waste reservoir 32, at the same time as isolating the sensing chamber (i.e. in the arrangement of FIG. 2, the upstream purge port 34 is not so connected to the downstream waste 32, but increasing the length of the valve channel 31B could result in such a connection). When such a connection is made, it is possible to either fill the waste from the breather port 58 (i.e. so that any liquid spills from the purge port 34) or to fill the waste from the purge port 34 (i.e. so that any liquid spills from the breather port 58). Further, the waste may be emptied by withdrawing liquid from either of the purge port 34 or the breather port 58 (assuming the other one is open).

Figure 9:
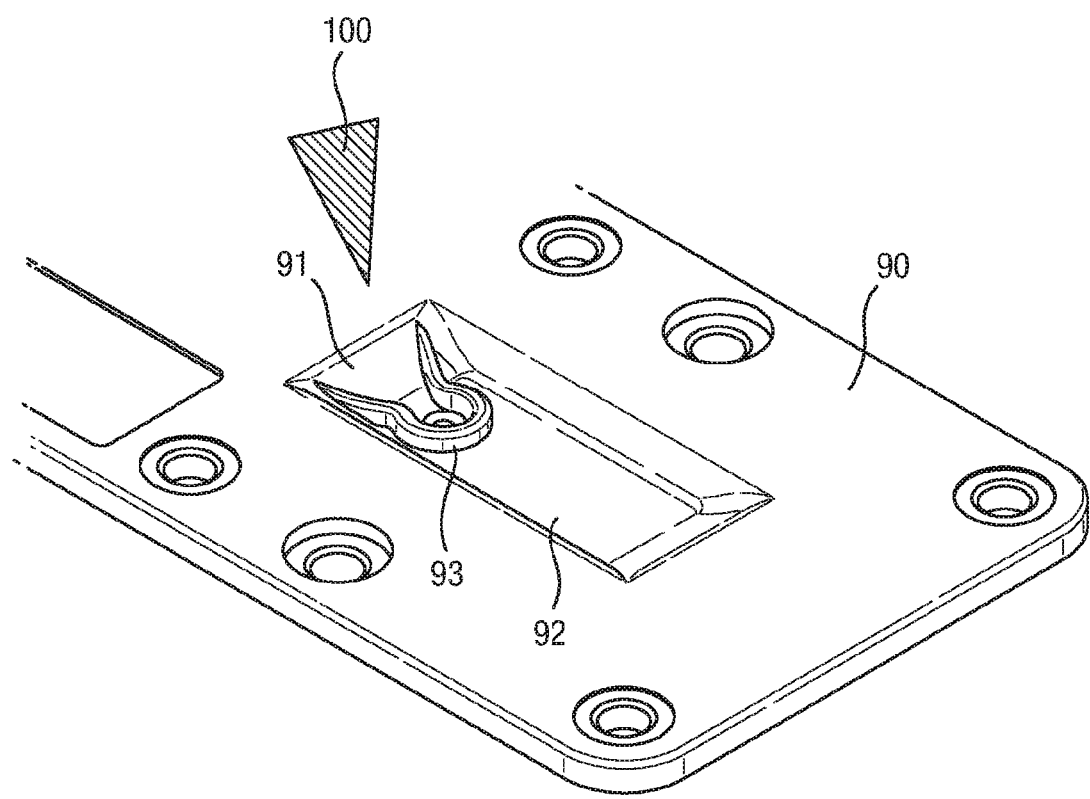
FIG. 9 shows an example design of a guide channel to guide a pipette to the sample input port.

FIG. 9 shows an example design of a guide channel 91 extending from the sample input port 92 of a portion of the device 90. The guide channel tapers outwardly from the port and serves to guide a pipette tip 100 applied to the channel to the sample input port. The guide channel also slopes downwardly towards the sample input port which aids travel of the pipette tip to the port. Once the pipette tip has been guided to the sample input port the user is able to apply liquid sample to the port from the pipette tip. Collar 93 serves to delimit the area of the channel and act as a support for a pipette tip applied directly to the sample input port. Due to the dimensions of the port, which may be for example be 1 mm or less in diameter, it may be challenging for the user to locate the pipette tip directly at the sample input port itself. The outwardly tapering channel area provides a larger target area for the user to locate and guide a pipette tip to the sample input port, should this be required.

Figure 10:
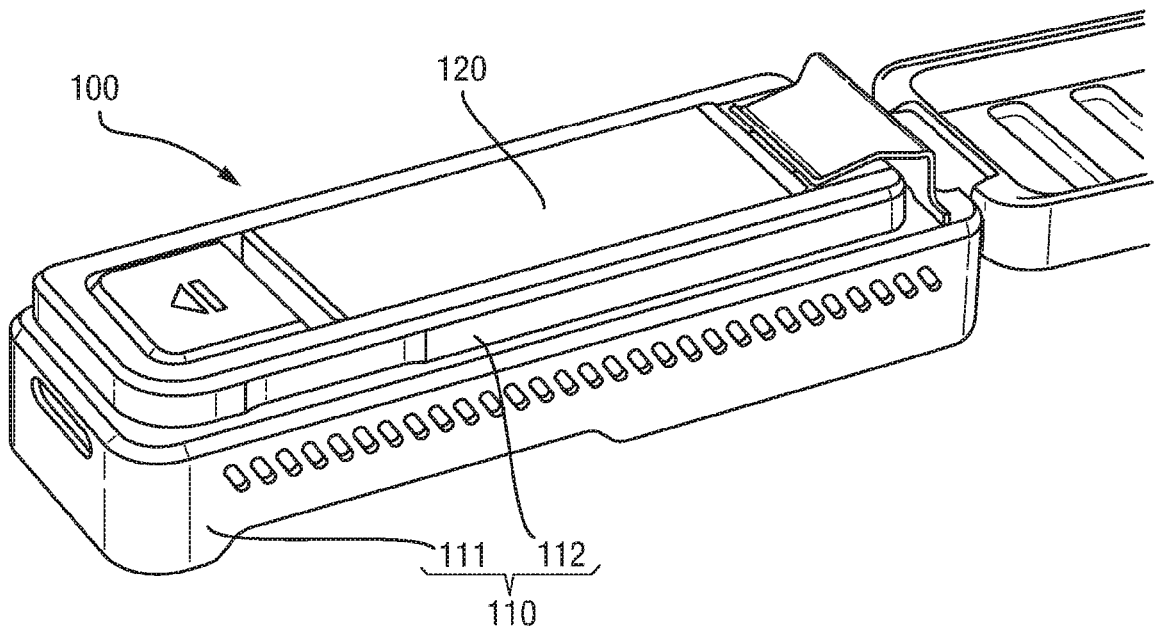
FIG. 10 shows a multi-part microfluidic device.
Figure 11:
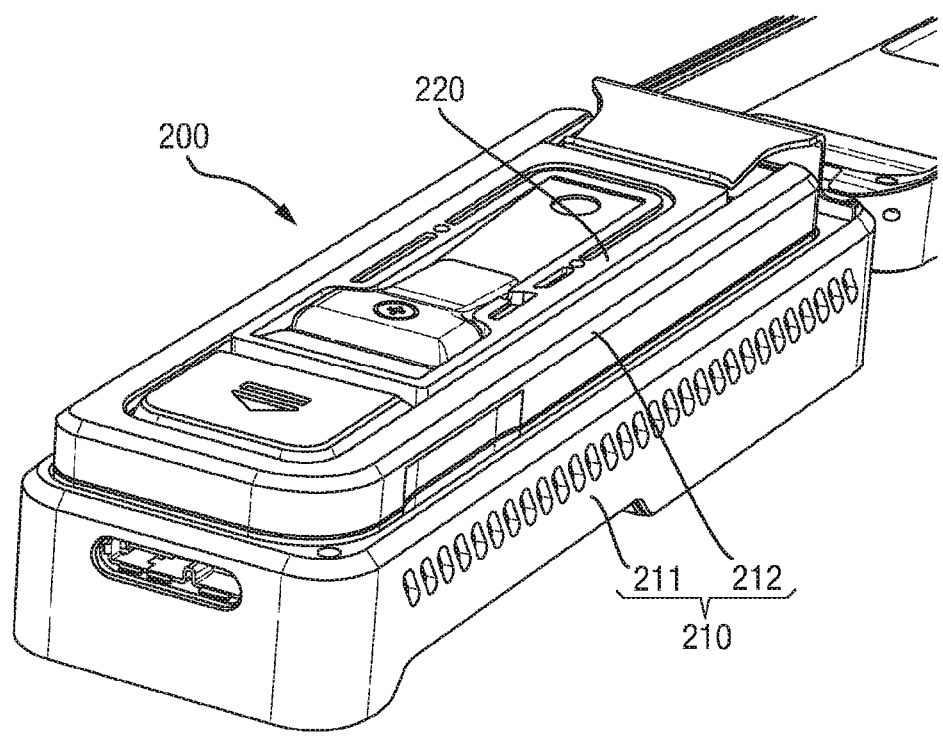
FIG. 11 shows an alternative multi-part microfluidic device.

FIG. 11 illustrates an apparatus similar to that of FIG. 10. The apparatus 200 has a first component 210 that forms the base of the device 200, whilst the second component 220 can be inserted and removed from the base component 210. The base component 210 itself can be composed of multiple components 211, 212. The first and second components 210, 220 each have respective arrays of electrical connectors that form a connection to each other when first and second components 210, 220 are connected. This allows multiple second components to be used with a single base component 210. The body of the second component 220 is typically made of a plastic material having a degree of elasticity. The plastic material may for example be polycarbonate.

Figure 12:
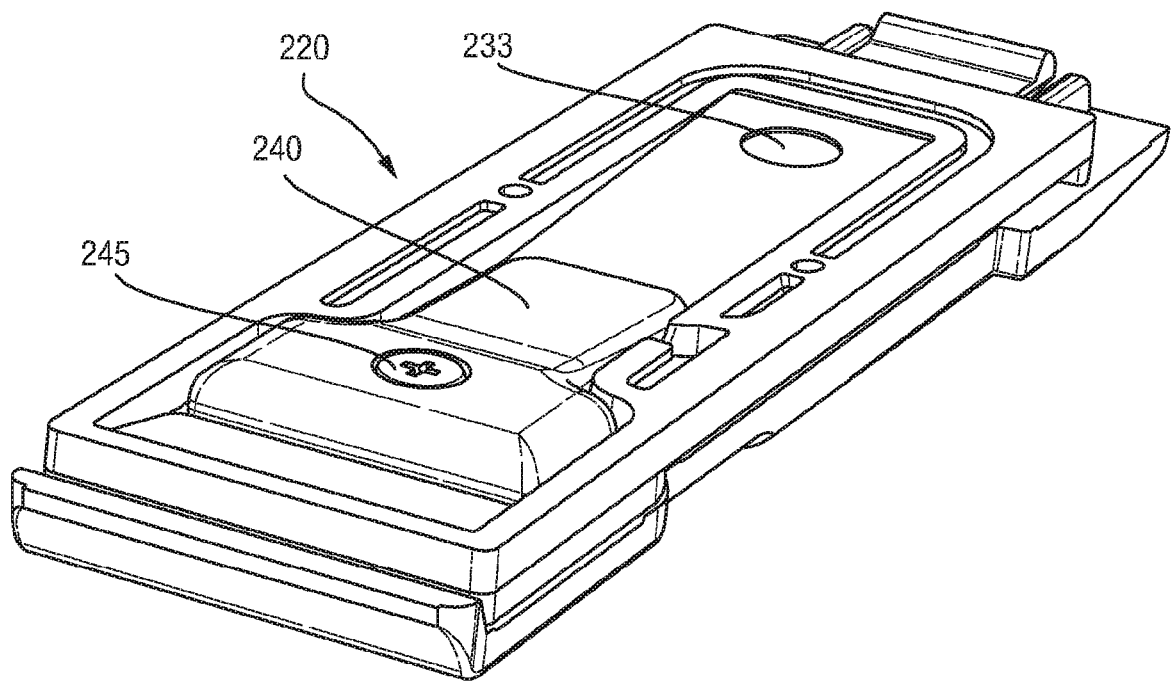
FIG. 12 shows a perspective view from above of a flow cell component of the multi-part microfluidic device of FIG. 11.
Figure 13:
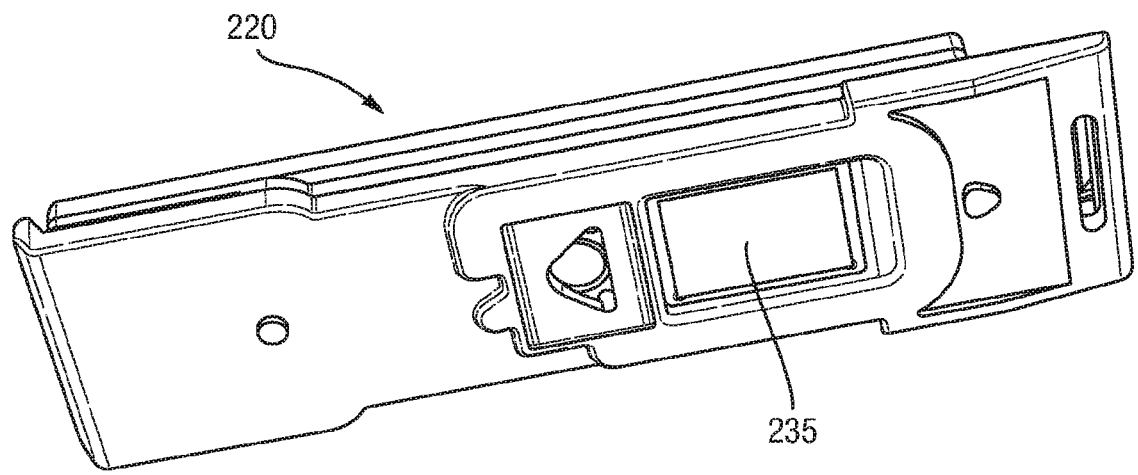
FIG. 13 shows a perspective view from below of a flow cell component of the multi-part microfluidic device of FIG. 11.

The second component 220 in FIG. 11 is a microfluidic apparatus, namely a flow-cell. Flow-cell 220 is shown in perspective views in FIGS. 12 and 13. FIG. 12 shows a view from above, whilst FIG. 13 shows a view from below. In FIG. 13, an array of connectors (not shown) form the bottom part of a sensor 235. The base 210 of FIG. 11 can have a corresponding array of electrical connectors to connect to the array on the flow cell 220.

Figure 14:
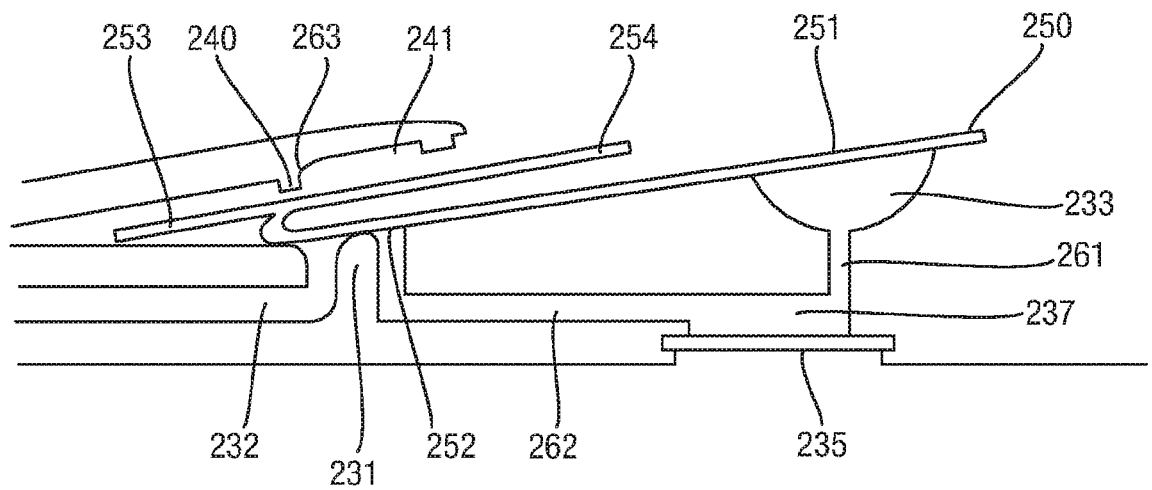
FIG. 14 shows a schematic cross-sectional view of a flow cell component of the multi-part microfluidic device of FIG. 11.

FIG. 14 shows a schematic cross-section through the flow cell 220. The sensor 235 is provided in a sensing chamber 237. Liquid (e.g. a buffer liquid or sample to be tested) can be supplied to the sensing chamber via an inlet channel 261. Similarly, liquid can leave the sensing chamber through an outlet channel 262. The inlet channel 261 and the outlet channel 262 are separate channels, to allow continuous flow of fluid through the sensing chamber 237 from the inlet channel 261 to the outlet channel 262.

The flow cell 220 may be constructed such that the flow path through the device is made from materials with good liquid retaining properties. That is, the materials are substantially liquid-impermeable, and can also be non-porous. This applies in particular to the upstream portion comprising the wetted volume before activation—i.e. the portion including the inlet channel 261, the chamber 237 and the outlet channel 262. Downstream portions, such as the bridging channel discussed below, do not require such high liquid retaining properties as they are not exposed to the fluid until after activation. In any case, examples of suitable barrier materials include cyclic olefin copolymer (COC) or cyclic olefin polymer (COP), which are rigid with high clarity. Other suitable materials, although softer and translucent rather than clear, include polyethylene (PE) and Polypropylene (PP) based materials. However, the flow cell 220 may also include additional coatings, co-extrusions, laminates or portions made from lower barrier materials (optionally combined with a secondary barrier as part of the device packaging). That is, the surface of the flow path can be made from materials with good liquid retaining properties, and the surrounding materials may be different.

Inlet channel 261 communicates with a reservoir 233 which acts as a sample input port to the flow cell 220. In other words, the reservoir 233 (when first seal 251 is removed, see below) is open to the surroundings of the flow cell 220, as can be seen in FIG. 12. This allows a user to place a sample to be tested in the reservoir 233, in an active state of the flow cell 220. By providing a large (e.g. 5 mm in diameter) port 233, it is easy for a user to provide a sample to the input port 233 without introducing any gas into the flow cell 220.

That is, the port 233 geometry is such that it provides a reservoir during the in-activated state (before the seals 251 and 252 are removed, see below). It can also provide a reservoir momentarily if or when sample is added, during the activated state, faster than it can be drawn into the flow cell.

Once activated, the liquid/air interface at the sample inlet end of the fluid path is biased to rest at the corner between the inlet channel 261 and the port/reservoir 233. The liquid/air interface at the other end of the fluid path is free to sit along the waste channel 232, with its position defined by the volume of fluid. Due to the capillary actions, this remains the case even if the cell fluid evaporates, regardless of which liquid/air interface the evaporation occurs at—the interface at the sample inlet end remains static while the waste end retracts as fluid volume reduces.

To add sample to the flow cell 220, a user need only contact the sample with the liquid/air interface at the sample inlet end (i.e. at the transition between the inlet channel 261 and the port/reservoir 233). This can either be directly, or by adding the sample into the reservoir forming region for the port 233, and allowing the sample to move (e.g. under gravity flow) towards, and contact, the interface. The sample inlet port 233 has an inlet diameter larger than a droplet diameter and may be advantageously dish shaped. Thus a droplet may be added to the device is able to move to the bottom of the dish by gravity and contact the fluid at the top of the inlet channel 261 at the interface with the sample inlet port. The tapered sides of the sample inlet port 233 allow the droplet to become focused at the inlet channel and minimise the introduction of a gas into the flow-cell by preventing a void forming. The sample inlet port 233 could also be of a shape other than dish shaped, for example a shallow cone.

Figure 18:
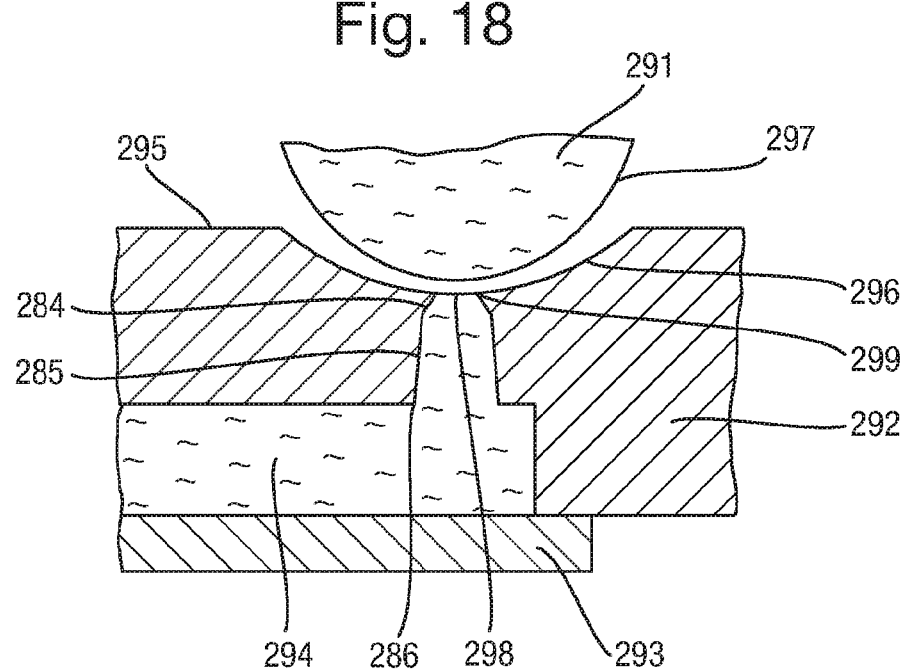
FIG. 18 is a schematic cross-sectional view of the addition of a sample to a sample port.

Addition of a sample is further illustrated in FIG. 18, which shows a sample fluid 291, a flow cell moulding 292, a sensor 293, and a cell fluid 294. A seal surface 295 has a sample port opening/reservoir 296 with a radius greater than sample droplet radius 297. This allows sample fluid 291 to contact the cell fluid air interface 298, rather than bridging over opening and trapping an air void between the fluid interfaces. Cell fluid air interface 298 is biased to rest at transition point 298 by capillary action due to pinning at the sharp circular edge 299 formed by a shutout surface in the mould tool during manufacturing. If cell fluid air interface 298 is forced away from edge 299, the tapers of surfaces 284 and 285 towards edge 299 increase the capillary force acting to return cell fluid air interface 298 back to edge 299. In an extreme case of cell fluid air interface 298 being forced away from edge 299, pinning at edge 286 adds Laplace bubble pressure to resist air being drawn further towards sensor 293.

Because the reservoir 233 is on the top face of the flow-cell 220, it is above the sensor 235. However, this is not necessary, either in a direct sense (i.e. the reservoir does not need to be directly over the sensing chamber) or in an absolute sense (i.e. the reservoir does not need to be a position that is more elevated than the sensing chamber), because liquid is drawn through the device by capillary flow as explained below. The reservoir 233 may be positioned at the same height or below the sensing chamber 237.

The flow-cell 220 is also provided with a waste liquid collection channel 232. In use, liquid exiting the sensor chamber 237 via the outlet channel 262 is received by the collection channel 232.

However, immediately between the outlet channel 262 and the collection channel 232 is a flow barrier 231. The flow barrier 231 is a wall that divides the outlet channel 262 from the collection channel 232. In other words, in the absence of the barrier 231, the flow path upstream of the barrier 231, finishing with the outlet channel 262 and the flow path downstream of the barrier 231, starting with the collection channel 232, would be directly connected to each other. The barrier 231 (and thus the end of the outlet channel 262) rises above the height of the sensing chamber 237 in the construction shown. However, this is not necessary because liquid is drawn through the device by capillary flow as explained below.

In an active or activated state, liquid can pass over the barrier 231 and pass into the waste collection channel 232. However, as shown in FIG. 14, the flow cell is in an in-active state. In this state, a first seal 251 covers the sample input port 233, whilst a second seal 252 covers the end of the sensing chamber outlet channel 262. In the illustrated embodiment, first and second seals 251, 252 are both provided as part of the same overall seal element 250. As shown, the overall seal element 250 may also cover the entrance to the waste collection channel 232 in the in-active state. The seal element 250 may be attached to the surface of the flow cell 220 by a glue that is more or less hydrophilic than the surface. In particular, such glue may be left behind when the first and second seals 251, 252 are removed, thereby imparting favourable wetting properties to the surface (e.g. discouraging flow of liquid out of the reservoir 233 or encouraging flow of liquid into the bridging channel 241 that is discussed below).

The end of the outlet channel 262 and the entrance to the waste collection channel 232 may be connected in the active state, over the barrier 231, via a barrier cover 240. The barrier cover 240 may comprise a bridging channel 241 for connecting the outlet channel 262 and the collection channel 232, and is discussed in further detail below.

The sealing element 250 may further comprise a release liner section 253. The release liner 253 is attached to the second seal 252. Release liner 253 can both extend beyond the second seal 252 (as illustrated, extending further beneath the barrier cover 240) and also double back over the seal to include a handle portion 254.

In this arrangement, pulling handle 254 provides a simple way to remove both seals 251 and 252. That is, by pulling handle 254, release liner 253 is pulled back from beneath the barrier cover 240 as the seal 252 is also pealed back in the same direction. In this way, any adhesive remaining on the lower side of the second seal 252 does not come into contact with the barrier 240 as it is peeled back and exposed, but is instead covered by the release liner 253 as it is simultaneously pulled back from beneath the barrier cover 240 with the second seal 252. As the handle 254 is pulled further, the first seal 251 is also removed from the sample input port 233.

The barrier cover 240 is preferably sprung, so that it is urged towards the main body of the flow-cell 220. As shown in FIG. 12, the barrier cover 240 may be biased into place by a fixing means such as a bolt or screw 245. In other arrangements the barrier cover 240 may be formed as a single piece with the body forming the fluidic channels. In either arrangement, the cover 240 may be flexible to allow the second seal 252 to be removed and for the cover 240 to then adjust and bear against the exposed surface beneath the seal 252.

Figure 15:
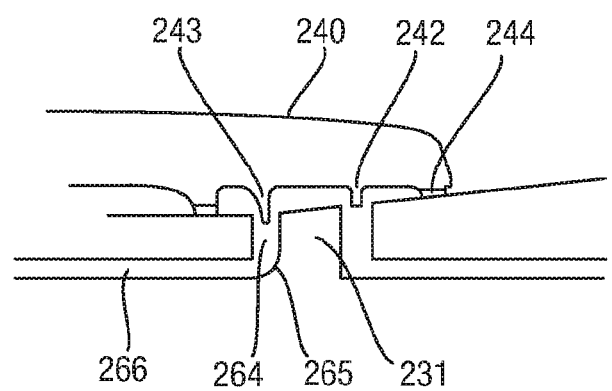
FIG. 15 shows a schematic cross-sectional view of a barrier cover element of the flow cell component of the multi-part microfluidic device of FIG. 11.

As a result, when the seal element 250 is removed, the bridging channel 241 of the barrier cover 240 is urged into place to form a connecting channel between the outlet channel 262 and the waste collection channel 232. The bridging channel 241 may be surrounded by a gasket 244, as shown in FIG. 15, to ensure a good seal between the outlet channel 262 and the waste collection channel 232. However, a seal may also be created without a gasket, via pinning of the fluid around the perimeter of the bridging channel 241. Alternatively, the barrier cover 240 may have a main body made of a sprung material (e.g. metal or a suitable plastic material), but the bridging channel 241 may be made of another material that facilitates making a seal, such as an elastomeric material. Such materials can be thermoplastic elastomers (TPEs) such as Thermolast K TF2 ATL from Kraiburg TPE GmbH & Co (Waldkraiburg, Germany), silicones, thermoplastic vulcanizates (TPVs) or thermoplastic polyurethane (TPU) for example. This effectively incorporates the gasket into the bridging channel 241.

Therefore, once the sealing element 250 has been removed, a continuous flow path through the flow-cell 220 is formed from the port 233, through the inlet channel 261 to the sensor chamber 237, then to the outlet channel 262 and through the bridging channel 241 into the waste collection channel 232. The completion of this flow path between the upstream and downstream portions either side of the barrier 231 puts the flow-cell 220 into an "active state". That is, the active state is one in which liquid can pass from the input port 233, through the sensor chamber and into the waste collection channel 232. The bridging channel 241 has a capillary dimension such that liquid passes from the collection channel 232 to the outlet channel 262.

Before the sealing element 250 is removed (and thus first and second seals 251, 252 are still in place), the flow-cell 220 is in an "in-active state". In that state, there is a sealed fluidic volume, or "saturated volume", formed from the first seal 251, through the closed-over input port 233, the inlet channel 261, the sensing chamber 232 and the outlet channel 262 to the surface of the second seal 252. In other words the flow path upstream of the barrier 231 is enclosed. In the in-active state, the flow cell is filled with a liquid from the first seal 251 at the sample input port 233 to the second seal 252 at the end of the sensing chamber outlet channel 262. By having that volume filled with liquid, such as a buffer liquid, the sensor 235 is prevented from being exposed to a gas or gas/liquid interface. This in turn protects the delicate components of the sensor 235, such as any membranes provided with nanopores for example.

The benefit of providing an in-active state in which the flow cell 220 is filled with liquid from the first seal 251 to the second seal 252 is that the flow-cell can be prepared for use and then readily transported without disrupting the sensor array. In particular, by excluding any gas, and therefore any gas/liquid interface, from the internal volume, there is no chance of a bubble disrupting the sensor 235 surface as the flow cell 220 is moved about and potentially changed in orientation during transportation.

In contrast, configuring the flow cell to the "active" state by removing the sealing element 250, allows sample to be added to the port 233, and liquid can flow through the sensing chamber 237 and into the waste collection 232. Nonetheless, the arrangement of the input port 233 and the barrier 231 with respect to the sensing chamber 237 means that liquid will not drain freely from the sensing chamber 237 even in the active state. This is because the dimensions of the input and output channels 261, 262 mean that capillary forces dictate the movement of the fluid.

That said, the initial removal of the sealing element 250 can cause some liquid to flow from the original saturated volume, i.e. out of the outlet channel 262, and into the bridging channel and potentially into the waste channel 232. In other words, the removal of the scaling element 250 can have a 'priming' effect, drawing some liquid through the device. However, such priming will not result in the free flow of fluid with the result that the sensing chamber 23 drains, due to the balance of the capillary forces.

In use, liquid is drawn into the inlet channel 261 from the reservoir 233 by capillary action. To assist with drawing fluid through the flow cell 220, particularly out of the outlet channel 262 and into the bridging channel 241, the barrier cover 240 can be provided with dippers 242 and 243, which are projections that can be, for example, circular in profile, although other shapes are possible. First dipper 242 extends from the barrier cover 240, through the bridging channel 241 and into the outlet channel 262. Second dipper 243 extends from the barrier cover 240, through the bridging channel 241 and into and waste collection channel 232. In some embodiments, only a dipper 242 into the outlet channel 262 may be provided. In other embodiments only a dipper 243 into the waste collection channel 232 may be provided. In other embodiments, as shown, both dippers 242 and 243 may be provided.

The dippers 242 and 243 help overcome any meniscus "pinning" that may counteract the capillary action during the flow of liquid through the cell 220. In other words, as liquid approaches the end of the outlet channel 262, the dipper penetrates into the liquid before the meniscus reaches the end of the outlet channel 262. This assists with the capillary action continuing to draw the liquid into the bridging channel 241. Similarly, the provision of the dipper 243 helps introduce the fluid into the collection channel 232 without the liquid undergoing meniscus pinning at the entrance to the liquid collection channel 232.

Flow from the bridging channel 241 into the waste collection channel 232 can also be assisted by providing a rounded corner at the end of the bridging channel 241, thereby reducing the number of sharp edges and therefore the potential for pinning. This rounded corner 263 is shown in FIG. 14, and the rounded edges at the entry to the downcomer 264 (which also assist with progression of liquid into the channel) can also be seen. Similarly, a rounded corner 265 can be provided between the downcomer 264 of the waste collection channel 232 (i.e. the entry portion of channel 232 next to the barrier 231) into the main channel 266 of the waste collection channel 232. This is illustrated in FIG. 15. The rounded corner 265 is provided opposite a sharp edge/corner on the other side of the channel. Although the corner 265 is rounded, the cross-section of the channel in a direction perpendicular to the direction of flow can be rectangular. This combination allows fluid to pin on the sharp edge whilst the fluid can progress around the bend with it resisting flow. This is because, with one contact point pinned, the fluid can form its native contact angle with the curved surface without "stretching" the exposed fluid surface (i.e. requiring work to be done on the surface) as it progresses along the channel.

Figure 16:
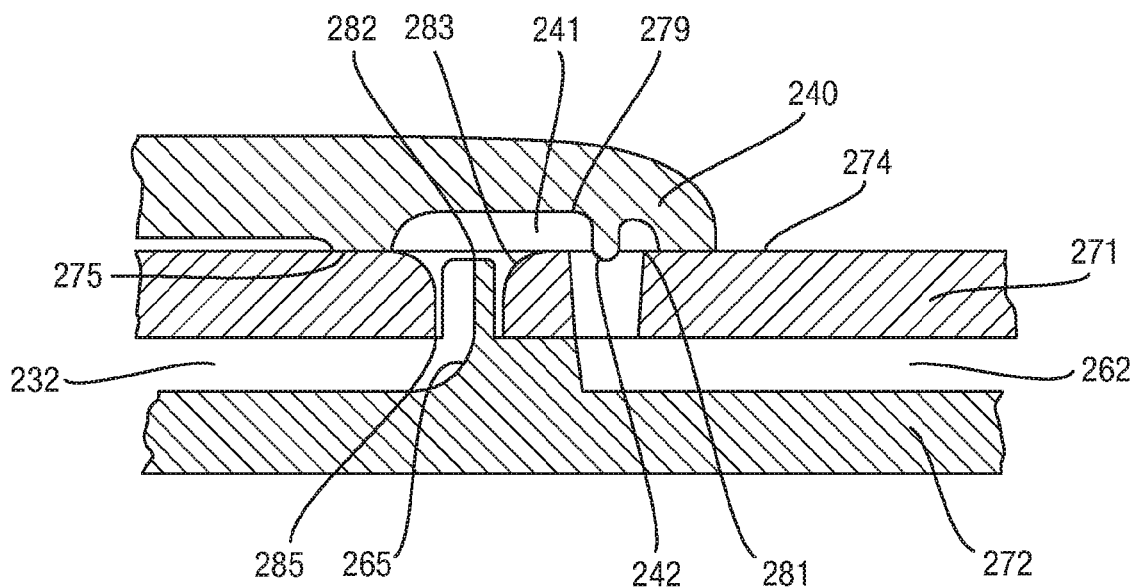
FIG. 16 shows a schematic cross-sectional view of an alternative barrier cover element of a flow cell component.

FIG. 16 shows an alternative arrangement to that of FIG. 15, with only one dipper 242. Additional detail of how the channels are formed from upper and lower moulded pieces—flow cell assembly moulding upper 271, and flow cell assembly moulding lower 272—is also shown. The figure shows the configuration after sealing element (not shown) has been removed from the sealing surface 274 (N.B. sealing surface 274 runs continuously from left to right in figure, although apparently interrupted in the particular section passing through the ports). Seal 275 is made between barrier cover 240 and flow cell upper moulding 271, enclosing a bridging channel 241 between cell outlet channel 262 and waste inlet channel 232. The surface 279 of the bridging channel can be hydrophilic to assist capillary action. A dipper 242 is formed by a protrusion of the barrier cover 240, which crosses the seal surface 274 and contacts the cell fluid air interface pinned at edge 281. A protrusion 282 of the flow cell assembly moulding lower 272 extends up into the port in the Flow cell assembly moulding upper 271, but does not cross the seal surface 274, allowing the sealing element to sit flat against the seal surface 274. However, the radius 283 prevents pinning so that cell fluid can progress along the surface 274 and make contact with protrusion 282. Once fluid has made contact with the flow cell assembly moulding lower at protrusion 282, capillary action draws it down a continuous surface, which has a radius 265 such that pinning at flow cell assembly moulding upper edge 285 does resist progression of the fluid front along the channel.

To further assist with the flow around the barrier 231, the bridging channel 241 and/or the surface of the barrier facing the bridging channel 241 may be provided with suitable surface wetting characteristics. This may also apply to the waste channel, to avoid the flow of liquid through the device becoming pinned in the waste channel. To encourage capillary action, the contact angle within the flow path is preferably less than 90°. Therefore, the surfaces in question may have a wetting contact angle of 90° or less with water. Optionally, the surfaces can be more hydrophilic than that to account for changes in sample wetting properties compared to pure water, for example having a wetting contact angle of 75° or less with water.

However, in some arrangements it may be desirable to ensure these surfaces are not too hydrophilic, to avoid the resultant capillary effect overcoming fluid retention at the input port and drawing liquid through the device and allowing air ingress, potentially exposing the sensor. Considering the arrangement of FIG. 5c and the balance of pressures discussed above, it can be considered that a contact angle of zero occurs at the at the inlet to cause minimum bubble radius, from which it can be shown that air ingress will only occur if the waste channel has a smaller effective radius than the input port (assuming fluid surfaces are at same height). In practice, the waste channel can have an effective radius at least double the size of the inlet port. Nonetheless, the device is not always level, and so the effect of hydrophilic or low contact angle waste surfaces is to reduce the head of pressure that can be tolerated as a result of tilting the device. As a result, the contact angle is optionally 10° or more with water, further optionally 20° C. or more.

The surface properties may be controlled by physical or chemical treatment. This applies in particular to the bridging channel 241, as it is readily accessible during production, but may also apply to the other components such as the surface of the barrier facing the bridging channel 241 and the waste channel, as discussed above.

In terms of physical treatment, the bridging channel 241 may be designed to have an increased capillary effect by increasing the area of hydrophilic surface to overcome local areas of hydrophobicity. That is, the surface area may be increased compared to a flat/untextured surface. This can be achieved by texturing, e.g. on the surface facing the barrier 231, to provide microscopic roughness and/or macroscopic features. Such macroscopic features could be provided as pillars, fins or channels/grooves for example. Additionally or alternatively a non-periodic and non-deterministic pattern could be created on said surface. Such microscopic features could be provided by forming the surface of the bridging channel with a moulding tool having a spark finish and/or by etching the surface. Such features may be around 0.2 mm deep, for example. Such features can by produced as part of the mould for the bridging channel 241.

Another form of physical treatment may include providing a physically porous element in the bridging channel 241. Such an element could assist with wicking liquid into, and subsequently through, the bridging channel 241. Such an element could fill the bridging channel 241. Such an element could be a sponge, e.g. formed of cellulose, or made of fabric or fibres. In some embodiments the porous element may dissolve in the liquid flowing through the device (after the seal is removed), as it will have served its purpose once the liquid has been assisted through the bridging channel.

In terms of chemical treatment, the bridging channel 241 may be coated with a suitable chemical to increase the hydrophilicity of the channel. Such chemicals may be commercial hydrophilic coatings, typically applied in a carrier solvent which evaporates to leave a layer of hydrophilic component behind, such as P100 and S100 from Jonnin (Gørløse, Denmark). Other solutions that evaporate to leave a layer of hydrophilic component behind, such as salt solutions, can also be used.

Another form of chemical treatment could be achieved by providing a layer of a different material, such as a solid or gel layer, between the seal and the upper surface of the barrier 231, the additional layer being of a more hydrophilic material than the underlying material of the 231. The additional layer could be bonded or fused to the underlying material substrate, or could be over-moulded. An advantage of this approach is that the different materials can provide different benefits—e.g. the main substrate could be a material with good water vapour barrier properties, to ensure the necessary fluid containment within the device, whilst the additional layer can be made of a more hydrophilic material than the substrate (as materials with good vapour barrier properties are often relatively hydrophobic rather than hydrophilic) to encourage flow over the barrier 231. Examples of this approach include using moulded Nylon 6 (polycaprolactam), which exhibits a contact angle with water of around 63°, as the additional layer, or a thin sheet of PET (polyethylene terephthalate) which exhibits a contact angle with water of around 73°. Other materials exhibiting suitable hydrophilic properties include polyvinyl alcohol (PVOH), with a contact angle of around 51°, polyvinyl acetate (PVA), with a contact angle of around 61°, polyethylene oxide (PEO)/polyethylene glycol (PEG), with a contact angle of around 63°, Nylon 6,6, with a contact angle of around 68°, Nylon 7,7, with a contact angle of around 70°, polysulfone (PSU), with a contact angle of around 71°, polymethyl methacrylate (PMMA), with a contact angle of around 71° or Nylon 12, with a contact angle of around 72°.

The balance of capillary forces across the flow cell 220 means that fluid does not freely flow into the bridging channel 241 and waste collection 232 from the sensing chamber, without some additional driving force. That driving force may be the provision of additional fluid to the inlet port 233. It may also be the presence of fluid in the inlet port reservoir 233 at the time the seal 251 is removed. In either case, such flow only occurs until the upstream liquid/air interface comes to rest at the transition between the inlet channel 261 and the port/reservoir 233, due to the balance of capillary forces as discussed above. As such, activating the flow cell 220 does not expose the sensor 235 to gas or a gas/liquid interface. In other words, activating the flow cell 220 does not cause liquid to drain through the flow cell 220 such that the sensor chamber 237 empties and exposes the sensor 235 to air. In addition, further protection against air ingress into the cell 220 is provided by fluid pinning at the edge between chamber 237 and inlet channel 261, e.g. during excessive tilting or acceleration of the flow cell 220. Once such transient events have concluded, the interface will move from this edge back to the transition between the inlet channel 261 and the port/reservoir 233, via capillary action.

Figure 17A:
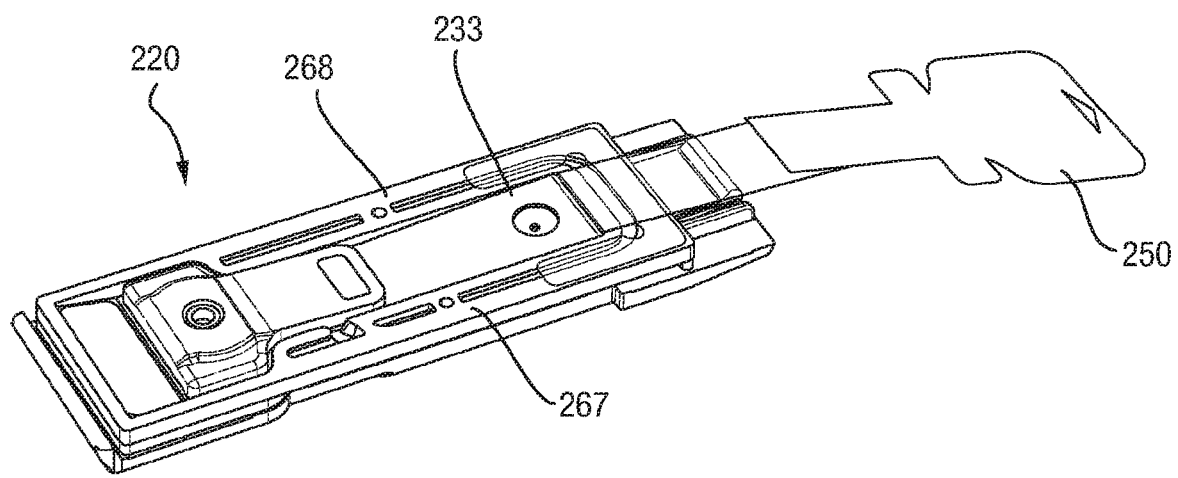
FIG. 17 shows a perspective view from above of a flow cell component with a seal removed in FIG. 17a, and replaced in FIG. 17b.
Figure 17B:
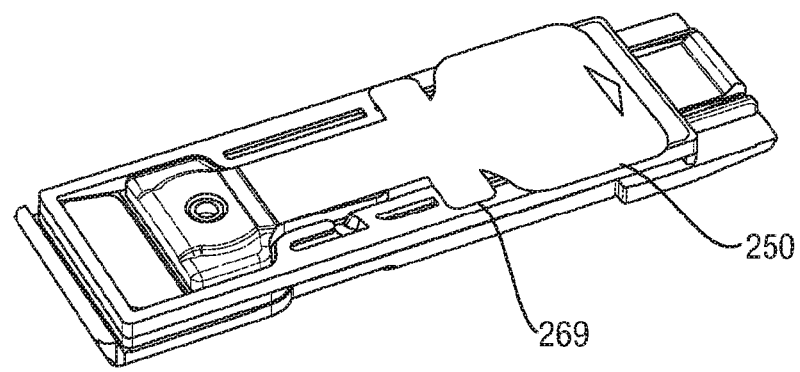

Following sample addition, the seal can be replaced over the sample port and waste ports to reduce evaporation. This is shown in FIG. 17. FIG. 17a illustrates a cell 220 with the seal element 250 removed, to expose the sample port 233. It also illustrates a fluid waste port 267, and an air waste port 268. These ports allow fluid to be drawn out of and removed from the flow cell 220 completely. Port 267 acts as an access point to remove fluid from the waste channel 232. As fluid is removed, despite the fluid being in communication with the sensor 235, air preferentially replaces the extracted fluid from downstream, via the port 268, rather than the fluid from the upstream sensor chamber 237 and sample port 233. FIG. 17b illustrates how the seal element 250 can be replaced, after the sample is supplied to port 233, to reduce evaporation and to protect the port 233 from contamination. The seal element 250 may also have waste port covers 269, which similarly help reduce evaporation from the ports 267, 268 and also help prevent contamination. The seal may have a transport window in the region of the sample port and/or waste port, to assist with port inspection.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

The invention claimed is:

1. A microfluidic device for analysing a test liquid comprising:
   a bridgeable barrier;
   an upstream portion, positioned upstream from the bridgeable barrier, for receiving a test liquid to be analysed, said upstream portion comprising an inlet channel and an outlet channel, and being fillable with a liquid between the inlet channel and the outlet channel;
   a sample input port in fluid communication with the inlet channel;
   a first removably attachable seal, configured to cover the sample input port;
   a sensor provided in a sensing chamber and housed in the upstream portion;
   a downstream portion, positioned downstream from the bridgeable barrier, for receiving liquid from the outlet channel of the upstream portion;
   a second removably attachable seal, configured to enclose the upstream portion and, when a liquid is provided in the upstream portion,
     inhibit flow of the liquid before removal of the second removably attachable seal, and
     after removal of the second removably attachable seal, permit liquid to pass the barrier from the upstream portion to the downstream portion;
   wherein the first and second removably attachable seals are configured to be pulled and removed together.

2. A microfluidic device according to claim 1, wherein a bridge is provided adjacent the barrier, and wherein after removal of the seal the bridge facilitates liquid to flow from the upstream portion to the downstream portion via or over the barrier.

3. A microfluidic device according to claim 2, wherein a surface of the bridge facing the barrier has a wetting contact angle of 90° or less with water.

4. A microfluidic device according to claim 3, wherein the surface of the bridge facing the barrier has a wetting contact angle of 75° or less with water.

5. A microfluidic device according to claim 3, wherein the surface of the bridge facing the barrier has a wetting contact angle of 20° or more with water.

6. A microfluidic device according to claim 3, wherein the surface of the bridge facing the barrier is provided with a chemically hydrophilic layer or treatment.

7. A microfluidic device according to claim 6, wherein the surface of the bridge facing the barrier is provided with a layer more hydrophilic than an untreated surface of the bridge or a plasma treatment.

8. A microfluidic device according to claim 3, wherein the surface of the bridge facing the barrier comprises a physical texture for increasing the surface area of the surface.

9. A microfluidic device according to claim 8, wherein the surface of the bridge facing the barrier comprises pillars, fins and/or grooves provided on the surface.

10. A microfluidic device according to claim 1, wherein the upstream portion is filled with liquid between the inlet channel and the outlet channel.

\* \* \* \* \*